US007919527B2

(12) United States Patent
Gainer et al.

(10) Patent No.: US 7,919,527 B2
(45) Date of Patent: Apr. 5, 2011

(54) BIPOLAR TRANS CAROTENOID SALTS AND THEIR USES

(75) Inventors: John L. Gainer, Charlottesville, VA (US); Raymond C. Grabiak, Maryland Heights, MO (US)

(73) Assignee: Diffusion Pharmaceuticals LLC, Charlottesville, VA (US)

( * ) Notice: Subject to any disclaimer, the term of this patent is extended or adjusted under 35 U.S.C. 154(b) by 0 days.

(21) Appl. No.: 12/656,288

(22) Filed: Jan. 25, 2010

(65) Prior Publication Data
US 2010/0137436 A1 Jun. 3, 2010

Related U.S. Application Data

(60) Division of application No. 10/647,132, filed on Aug. 25, 2003, now Pat. No. 7,759,506, which is a continuation-in-part of application No. 10/372,717, filed on Feb. 25, 2003, now Pat. No. 7,351,844.

(60) Provisional application No. 60/358,718, filed on Feb. 25, 2002.

(51) Int. Cl.
*A01N 27/00* (2006.01)
(52) U.S. Cl. ........................................ 514/547; 560/190
(58) Field of Classification Search .................. 514/547; 560/190
See application file for complete search history.

(56) References Cited

U.S. PATENT DOCUMENTS

| 2,175,843 | A | 10/1939 | Kuhn et al. |
| 2,948,748 | A | 8/1960 | Guex et al. |
| 3,489,806 | A | 1/1970 | Gutmann et al. |
| 3,687,990 | A | 8/1972 | Gutmann et al. |
| 3,788,468 | A | 1/1974 | Gainer |
| 3,853,993 | A | 12/1974 | Gainer et al. |
| 3,965,261 | A | 6/1976 | Gainer |
| 3,975,519 | A | 8/1976 | Gainer |
| 4,009,270 | A | 2/1977 | Gainer, Jr. |
| 4,038,144 | A | 7/1977 | Gainer |
| 4,046,880 | A | 9/1977 | Gainer |
| 4,070,460 | A | 1/1978 | Gainer, Jr. |
| 4,105,855 | A | 8/1978 | Schulz et al. |
| 4,176,179 | A | 11/1979 | Gainer |
| 4,216,211 | A | 8/1980 | Francis |
| 5,472,946 | A | 12/1995 | Peck et al. |
| 6,060,511 | A * | 5/2000 | Gainer ..................... 514/558 |
| 6,150,561 | A | 11/2000 | Kreienbuhl et al. |
| 7,145,025 | B2 | 12/2006 | Lockwood et al. |
| 7,446,101 | B1 | 11/2008 | Madhavi et al. |
| 2003/0180282 | A1 | 9/2003 | Serebruany et al. |
| 2004/0109920 | A1 | 6/2004 | Reuscher et al. |
| 2006/0194973 | A1 | 8/2006 | Gainer et al. |
| 2007/0088248 | A1 | 4/2007 | Glenn et al. |
| 2008/0255246 | A1 | 10/2008 | Gainer |

FOREIGN PATENT DOCUMENTS

| CH | 522 572 | 6/1972 |
| EP | 0 908 449 | 4/1999 |
| EP | 0 908 449 A1 | 4/1999 |
| JP | 63-059831 | 3/1988 |
| JP | A 03-056412 | 3/1991 |
| JP | A 04-264020 | 9/1992 |
| JP | 05-032531 | 2/1993 |
| JP | A 05-178765 | 7/1993 |
| JP | 7-223960 | 8/1995 |
| JP | A 07/291854 | 11/1995 |
| JP | 10-502388 | 3/1998 |
| JP | 2002-524535 | 8/2002 |
| JP | A 03-26607 | 1/2003 |
| WO | WO 92/15544 | 9/1992 |
| WO | WO 9500130 | 1/1995 |
| WO | WO 98/14183 | 4/1998 |
| WO | WO 9814183 | 4/1998 |
| WO | WO 03/072734 | 9/2003 |
| WO | WO 03/072734 A2 | 9/2003 |
| WO | WO 2004/048323 | 6/2004 |
| WO | WO 2005/028411 | 3/2005 |
| WO | WO 2006/039685 | 4/2006 |
| WO | WO 2006/104610 | 10/2006 |
| WO | WO 2007/072529 | 6/2007 |

OTHER PUBLICATIONS

Notification Concerning Transmittal of International Preliminary Report on Patentability (Chapter 1 of the Patent Cooperation Treaty), dated May 14, 2010.
International Preliminary Report on Patentability, dated May 4, 2010.
Written Opinion dated Mar. 25, 2009 in PCT/US2008/012440 [previously submitted].
Johnson, M.E., et al, *Journal of Pharmaceutical Sciences*, vol. 85, No. 7, pp. 670-679, Jul. 1996, "Synergistic effects of chemical enhancers and therapeutic ultrasound on transdermal drug delivery."
Holloway, G.M., et al, The American Physiological Society, 1988, pp. 683-686—Department of Chemical Engineering, and Dept. of Anesthesiology, School of Medicine, Univ. of VA, Charlotteville, Va; "The carotenoid crocetin enhances pulmonary oxygenation."
Okonkwo, D.O., et al, Neuroscience Letters 352 (2003) 97-100, "Trans-sodium crocetinate increases oxygen delivery to brain parenchyma in rats on oxygen supplementation."
Seyde, Walter C., et al, Journal of Cerebral Blood Flow and Metabolism, vol. 6, No. 6, 1986, pp. 703-707, "Carotenoid Compound Crocetin Improves Cerebral Oxygenation in Hemorrhaged Rats."
Chinese Office Action and its English Translation dated Feb. 12, 2010 in the Assignee's Chinese application relating to PCT/US 06/06422.
Examination Report dated Apr. 7, 2010 issued by the New Zealand Patent Office in Applicants' corresponding foreign application No. 584433.
Wirz, R., et al, Helv. Chim. Acta, vol. 43, No. 6, 1960, pp. 1738-1745, (XP008042762).
Isler, O., et al, Helv. Chim. Acta, vol. 40, No. 5, 1957, pp. 1242-1249, (XP008042920).

(Continued)

*Primary Examiner* — Deborah D Carr
(74) *Attorney, Agent, or Firm* — Nixon & Vanderhye P.C.

(57) ABSTRACT

The invention relates to trans carotenoid salt compounds, methods for making them, methods for solubilizing them and uses thereof. These compounds are useful in improving diffusivity of oxygen between red blood cells and body tissues in mammals including humans.

27 Claims, No Drawings

OTHER PUBLICATIONS

Database Caplus, Chemical Abstracts Service, Columbus, Ohio, US; (XP002317165) [JP 63 059831].
Wenkert, E., et al, J. Org. Chem., vol. 55, No. 25, 1990, p. 6203-6214 (XP002317164).
Database Caplus, Chemical Abstracts Service, Columbus, Ohio, US; (XP002317166) [JP 05 032531].
Gibson, T.W., et al, J. Org. Chem., vol. 41, No. 5, 1976, pp. 791-793, (XP002325593).
Examination Report dated Apr. 12, 2010 issued by the India Patent Office in one of Applicants' corresponding foreign applications.
Pfander, H. et al, *Pure & Appl. Chem.*, vol. 69, No. 10, pp. 2047-2060 (1997), "Carotenoid synthesis: A progress report."
Widmer, Erich et al, Helvetica Chemica Acta—vol. 73 (1990), pp. 861-867, Technical Procedures for the Syntheses of Carotenoids and Related Compounds . . . .
Polish Office Action dated Feb. 23, 2010 from Polish Patent Application No. P-373780 based on PCT/US03/05521.
Australian Office Action dated Mar. 26, 2010 in applicant's Australian application No. 2003265617.
Wirz, R., et al, Helv. Chim. Acta, vol. 43, No. 6, 1960, pp. 1738-1745.
Wenkert, E., et al, J. Org. Chem., vol. 55, No. 25, 1990, pp. 6203-6214.
Chinese Office Action dated Mar. 29, 2010 from Chinese Patent Application No. 03826969.4 based on PCT/US03/26424.
Ladig et al, *J. Am. Chem. Soc.*, 120, 9394-9395 (1998).
Japanese Office Action and its English Translation dated Apr. 6, 2010 in the Assignee's Japanese application relating to PCT/US2006/006422.
Mexican Office Action dated May 2010, and English translation of rejected parts of the Office Action, from Mexican Patent Application No. PA/a/2004/008253 corresponding to International Patent Application No. PCT/EP2003/005521.
Canadian Office Action issued Oct. 26, 2010 in corresponding Canadian Application No. 2537210.
Examination Report dated Oct. 25, 2010 issued by the Australian Patent Office in one of Applicants' corresponding foreign applications.
Norwegian Office Action and its English Translation mailed Jun. 22, 2010 in the Assignee's Norwegian application relating to PCT/US03/05521.
Wirz, R., et al, Helv. Chim. Acta, vol. 43, No. 6, 1960, pp. 1738-1745, (XP008042762).
Database Caplus, Chemical Abstracts Service, Columbus, Ohio, US; XP002317165 [JP 63 059831].
Korean Office Action and its English Translation dated Jun. 22, 2010 from applicant's Korean Patent Appln. No. 10-2006-7003827, that corresponds to PCT/US03/26424.
Ukraine Office Action issued Aug. 2010.
Written Opinion and International Search Report issued in PCT/US06/06422 dated Oct. 19, 2006.
Database HCAPLUS on STN, DN 141:388250, Magesh, V. "Studies on the anti-tumor effect of crocetin against benzo(a)pyrene induced lung cancer in Swiss albino mice." Biomedicine, (Chennai, India) (2003), 23 (3 & 4), 96-99, Abstract.
Canadian Office Action issued Jul. 7, 2010 in corresponding Canadian Application No. 2477245.
Wirz, R., et al, *Helv. Chim. Acta*, vol. 43(6), pp. 1738-1745, 1960, (XP008042762).
Wenkert, E., et al, *J. Org. Chem.*, vol. 55(25), pp. 6203-6214, 1990, (XP002317164).
RN: 33261-80-2; CN: 2,4,6,8,10,12,14,16,18-Eicosanonaenedioic acid, 4,8,13,17-tetramethyl-dipotassium salt.
RN: 33261-81-3; CN: 2,4,6,8,10,12,14,16,18-Eicosanonaenedioic acid, 4,8,13,17-tetramethyl-disodium salt.
RN: 120523-11-7; CN: 2,4,6,8,10,12,14,16,18-Eicosanonaenedioic acid, 4,8,13,17-tetramethyl-potassium sodium salt.
RN: 147484-59-1; CN: 2,4,6,8-Decatetraenedioic acid, disodium salt.
Examination Report dated Oct. 7, 2010 issued by the New Zealand Patent Office in one of Applicants' corresponding foreign applications.
IPRP issued in corresponding PCT Appln. No. PCT/US2008/004708.
Polish Office Action dated Sep. 2010 in corresponding Polish Application No. P-373780.
International Search Report dated Sep. 1, 2010 in PCT/US 10/01794.
Written Opinion dated Sep. 1, 2010 in PCT/US 10/01794.
Supplementary European Search Report dated Apr. 29, 2010 issued by the EPO in one of Applicants' corresponding foreign applications.
Zheng, S., et al, "Crocetin Attenuates Atherosclerosis in Hyperlipidemic Rabbits Through Inhibition of LDL Oxidation," Journal of Cardiovascular Pharmacology, vol. 47, No. 1, Jan. 2006, pp. 70-76, XP009135396, ISSN: 0160-2446.
Supplementary European Search Report dated Apr. 29, 2010 issued by the EPO in one of Applicants' corresponding foreign applications.
Schwieter, U., et al, "Synthesen in der Carotinoid-Reiche 20. Mitteilung Neu Synthesen von Apocarotinoiden," Helvetica Chimica Acta, vol. 1, (1966), pp. 369-390, XP-002575142.
Korean Office Action and its English Translation dated Jul. 6, 2010 in the Assignee's Korean application 10-2004-7013118, that is the nationalized appln. from PCT/US03/05521, claiming priority from U.S. Appl. No. 60/358,718.

* cited by examiner

BIPOLAR TRANS CAROTENOID SALTS AND THEIR USES

RELATED APPLICATIONS

This application is a divisional of U.S. patent application Ser. No. 10/647,132, filed Aug. 25, 2003, now 7,759,506 which is a continuation-in-part of U.S. patent application Ser. No. 10/372,717, filed Feb. 25, 2003, now U.S. Pat. No. 7,351,844 which claims the benefit of U.S. Provisional Patent Application No. 60/358,718, filed Feb. 25, 2002, the entire contents of which are hereby incorporated by reference in this application.

FIELD OF THE INVENTION

The invention relates to bipolar trans carotenoid salt compounds, methods of solubilizing them, methods for making them, and methods of using them. These bipolar trans carotenoid salts (BTCS) compounds are useful in improving diffusivity of oxygen between red blood cells and body tissues in mammals including humans.

BACKGROUND OF THE INVENTION

Carotenoids are a class of hydrocarbons consisting of isoprenoid units joined in such a manner that their arrangement is reversed at the center of the molecule. The backbone (skeleton) of the molecule consists of conjugated carbon-carbon double and single bonds, and can also have pendant groups. Although it was once thought that the skeleton of a carotenoid contained 40 carbons, it has been long recognized that carotenoids can also have carbon skeletons containing fewer than 40 carbon atoms. The 4 single bonds that surround a carbon-carbon double bond all lie in the same plane. If the pendant groups are on the same side of the carbon-carbon double bond, the groups are designated as cis; if they are on opposite side of the carbon-carbon bond, they are designated as trans. Because of the large number of double bonds, there are extensive possibilities for geometrical (cis/trans) isomerism of carotenoids, and isomerization occurs readily in solution. A recent series of books is an excellent reference to many of the properties, etc. of carotenoids ("Carotenoids", edited by G. Britton, S. Liaaen-Jensen and H. Pfander, Birkhauser Verlag, Basel, 1995 hereby incorporated by reference in its entirety).

Many carotenoids are nonpolar and, thus, are insoluble in water. These compounds are extremely hydrophobic which makes their formulation for biological uses difficult because, in order to solubilize them, one must use an organic solvent rather than an aqueous solvent. Other carotenoids are monopolar, and have characteristics of surfactants (a hydrophobic portion and a hydrophilic polar group). As such, these compounds are attracted to the surface of an aqueous solution rather than dissolving in the bulk liquid. A few natural bipolar carotenoid compounds exist, and these compounds contain a central hydrophobic portion as well as two polar groups, one on each end of the molecule. It has been reported ("Carotenoids", Vol. 1A, p. 283) that carotenoid sulphates have "significant solubility in water of up to 0.4 mg/ml". Other carotenoids that might be thought of as bipolar are also not very soluble in water. These include dialdehydes and diketones. A di-pyridine salt of crocetin has also been reported, but its solubility in water is less than 1 mg/ml at room temperature. Other examples of bipolar carotenoids are crocetin and crocin (both found in the spice saffron). However, crocetin is only sparingly soluble in water. In fact, of all of the bipolar carotenoids, only crocin displays significant solubility in water.

U.S. Pat. Nos. 4,176,179; 4,070,460; 4,046,880; 4,038,144; 4,009,270; 3,975,519; 3,965,261; 3,853,933; and 3,788,468 relate to various uses of crocetin.

U.S. Pat. No. 5,107,030 relates to a method of making 2,7-dimethyl-2,4,6-octatrienedial and derivatives thereof.

U.S. Pat. No. 6,060,511 relates to trans sodium crocetinate (TSC) and its uses. The TSC is made by reacting naturally occurring saffron with sodium hydroxide followed by extractions.

In Roy et al, *Shock* 10, 213-7. (1998), hemorrhaged rats (55% blood volume) were given a bolus of trans sodium crocetinate (TSC) after the hemorrhage ended, followed by saline after another 30 minutes. All of the TSC-treated animals lived, while all controls died. Whole-body oxygen consumption increased in the TSC group, reaching 75% of normal resting value after. about 15 minutes.

Laidig et al, J Am Chem. Soc. 120, 9394-9395 (1998), relates to computational modeling of TSC. A simulated TSC molecule was "hydrated" by surrounding it with water molecules. The re-ordering of the water in the vicinity of the TSC made it easier for oxygen molecules to diffuse through the system. The computational increase in diffusivity of ~30% was consistent with results obtained in both in vitro and animal experiments.

In Singer et al, *Crit Care Med* 28, 1968-72. (2000), TSC improved hemodynamic status and prolonged rat survival in a rat model of acute hypoxia. Hypoxia was induced using a low oxygen concentration (10%) air mixture: after 10 minutes the animals were given either saline or TSC. Hypoxemia led to a reduction in blood flow, and an increase in base deficit. Only 2 of 6 animals survived in the control group. The treated group all survived with good hemodynamic stability for over two hours, with a slow decline thereafter.

SUMMARY OF THE INVENTION

The subject invention relates to bipolar trans carotenoid salts (BTCS) compounds and synthesis of such compounds having the structure:

YZ-TCRO-ZY where:
Y=a cation
Z=polar group which is associated with the cation, and
TCRO=trans carotenoid skeleton.

The subject invention also relates to individual BTCS compound compositions (including a TSC composition) wherein absorbency of the highest peak (of an aqueous solution of the BTCS composition) which occurs in the visible wave length range divided by the absorbency of the peak which occurs in the UV wave length range, is greater than 7.0, advantageously greater than 7.5, most advantageously greater than 8.

The invention also relates to a method of treating a variety of diseases comprising administering to a mammal in need of treatment a therapeutically effective amount of a compound having the formula:

YZ-TCRO-ZY

The invention also includes several methods of solubilizing and synthesizing compounds having the formula:

YZ-TCRO-ZY

The invention also relates to an inhaler for delivery of the compounds of the invention.

DETAILED DESCRIPTION OF THE INVENTION

A new class of carotenoid and carotenoid related compounds has been discovered. These compounds are referred to as "bipolar trans carotenoid salts" (BTCS).
Compounds of the Invention The subject invention relates to a class of compounds, bipolar trans carotenoid salts, that permit the hydrophobic carotenoid or carotenoid related skeleton to dissolve in an aqueous solution, and methods for making them. The cations of these salts can be a number of species, but advantageously sodium or potassium (these are found in most biological systems). Commonly owned U.S. Pat. No. 6,060,511, hereby incorporated by reference in its entirety, describes an extraction method for making trans sodium crocetinate, TSC (a BTCS) starting from saffron.

A general structure for a bipolar trans carotenoid salt is:

YZ-TCRO-ZY where:
Y (which can be the same or different at the two ends)=a cation, preferably $Na^+$ or $K^+$ or $Li^+$. Y is advantageously a monovalent metal ion. Y can also be an organic cation, e. g., $R_4N^+$, $R_3S^+$, where R is H, or $C_nH_{2n+1}$ where n is 1-10, advantageously 1-6. For example, R can be methyl, ethyl, propyl or butyl.
Z (which can be the same or different at the two ends)= polar group which is associated with the cation. Optionally including the terminal carbon on the carotenoid (or carotenoid related compound), this group can be a carboxyl ($COO^-$) group or a CO group. This group can also be a sulfate group ($OSO_3^-$) or a monophosphate group ($OPO_3^-$),
($OP(OH)O_2^-$), a diphosphate group, triphosphate or combinations thereof.
TCRO=trans carotenoid or carotenoid related skeleton (advantageously less than 100 carbons) which is linear, has pendant groups (defined below), and typically comprises "conjugated" or alternating carbon-carbon double and single bonds (in one embodiment, the TCRO is not fully conjugated as in a lycopene). The pendant groups are typically methyl groups but can be other groups as discussed below. In an advantageous embodiment, the units of the skeleton are joined in such a manner that their arrangement is reversed at the center of the molecule. The 4 single bonds that surround a carbon-carbon double bond all lie in the same plane. If the pendant groups are on the same side of the carbon-carbon double bond, the groups are designated as cis; if they are on the opposite side of the carbon-carbon bond, they are designated as trans. The compounds of the subject invention are trans. The cis isomer typically is a detriment—and results in the diffusivity not being increased. In one embodiment, a trans isomer can be utilized where the skeleton remains linear.

Examples of trans carotenoid or carotenoid related skeletons are:

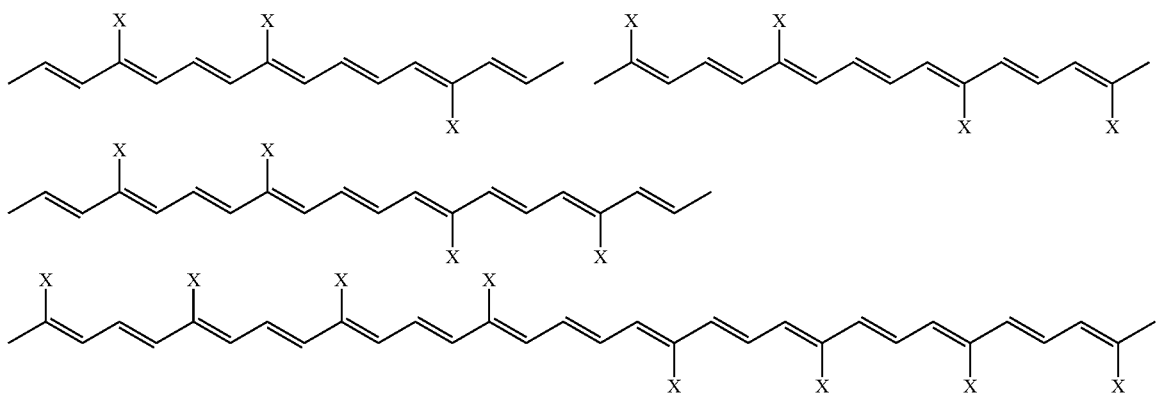

where pendant groups X (which can be the same or different) are hydrogen (H) atoms, or a linear or branched group having 10 or less carbons, advantageously 4 or less, (optionally containing a halogen), or a halogen. Examples of X are a methyl group ($CH_3$), an ethyl group ($C_2H_5$), a halogen-containing alkyl group (C1-C10) such as $CH_2Cl$, or a halogen such as Cl or Br. The pendant X groups can be the same or different but the X groups utilized must maintain the skeleton as linear.

Although many carotenoids exist in nature, carotenoid salts do not. Commonly owned U.S. Pat. No. 6,060,511 relates to trans sodium crocetinate (TSC). The TSC was made by reacting naturally occurring saffron with sodium hydroxide followed by extractions that selected primarily for the trans isomer.

The presence of the cis and trans isomers of BTCS can be determined by looking at the ultraviolet-visible spectrum for the carotenoid sample dissolved in an aqueous solution. Given the spectrum, the value of the absorbency of the highest peak which occurs in the visible wave length range of 416 to 423 nm (the number depending on the solvent used) is divided by the absorbency of the peak which occurs in the UV wave length range of 250 to 256 nm, can be used to determine the purity level of the trans isomer. When the BTCS is dissolved in water, the highest visible wave length range peak will be at about 421 nm and the UV wave length range peak will be at about 254 nm. According to M. Craw and C. Lambert, Photochemistry and Photobiology, Vol. 38 (2), 241-243 (1983) hereby incorporated by reference in its entirety, the result of the calculation (in that case crocetin was analyzed) was 3.1, which increased to 6.6 after purification.

Performing the Craw and Lambert analysis, using a cuvette designed for UV and visible wave length ranges, on the trans sodium crocetin of commonly owned U.S. Pat. No. 6,060,511 (TSC made by reacting naturally occurring saffron with sodium hydroxide followed by extractions which selected primarily for the trans isomer), the value obtained averages about 6.8. Performing that test on the synthetic TSC of the subject invention, that ratio is greater than 7.0 (e.g. 7.0 to 8.5), advantageously greater than 7.5 (e.g. 7.5-8.5), most advantageously greater than 8. For the TSC synthesized according to the improved method of Example 5, the ratio is greater than 7.4 (e.g. 7.4-8.5). The synthesized material is a "purer" or highly purified trans isomer.

It has been found, recently, that TSC has an aqueous solubility of around 10 mg/ml at room temperature, which is remarkable for a molecule containing such a long, hydrophobic portion. TSC has also been found to increase the diffusivity of oxygen through liquids.

U.S. Pat. No. 6,060,511 describes an extraction method for making TSC starting from saffron; however, other bipolar carotenoid salts cannot be made using that same procedure since the use of saffron allows only a single carotenoid skeleton to be incorporated into the salt.

The invention disclosed herein allows the synthesis of a whole class of compounds: bipolar trans carotenoid salts which contain various carotenoid or carotenoid related skeletons. Such compounds are soluble in aqueous solutions and have advantageous biological uses, such as causing an increase in oxygen utilization. It is believed that this increase is a result of the ability of the hydrophobic portion (the skeleton) of the bipolar trans carotenoid salt to affect the bonding of water molecules. This, in effect, allows the oxygen molecule to diffuse faster in that area.

Solubilizing the Compounds and Compositions of the Invention

The invention allows for the dissolution of a trans carotenoid or carotenoid related skeleton molecule in aqueous solutions. The novel methods of dissolution are related below. The methods apply to any bipolar trans carotenoid salt and composition thereof.

BTCS-containing Saline Infusion Solutions

Large volumes (as much as 3 times the estimated blood loss) of isotonic saline (also called normal saline) are infused as a treatment for hemorrhagic shock. The isotonic saline contains 9 g NaCl per liter of water so as not to disturb the ionic strength of the plasma once it is infused into the body. Adding TSC to the saline has been shown to result in a superior infusion fluid, however, one cannot simply mix TSC powder with the saline to make such a solution. About 50% of the TSC dissolves in normal saline no matter how much TSC is added (up to several milligrams per ml), which means that undissolved particles of TSC are still present. In order to prevent that, a stock solution can be made by adding more than twice the amount of TSC needed and then centrifuging out the particles that do not dissolve. The actual composition of the stock solution can be verified using UV-visible spectroscopy. This stock solution can be added to normal saline and the TSC remains dissolved.

This method can be used to dissolve a BTCS in other types of sodium chloride solutions, as well as in solutions of other salts such as KCl, $Na_2SO_4$, lactate, etc. Several, eg 1-3 mg/ml, can be put into solution in this manner.

Dilute Solution of Sodium Carbonate Dissolves BTCS

A BTCS such as TSC dissolves in very dilute sodium carbonate solutions. A dilute, eg 0.00001-0.001M, solution of sodium carbonate can be added, dropwise, to deionized water until the pH is 8.0 (the pH of deionized water is usually 5-6). This only takes a few drops of the very dilute sodium carbonate per, say, 50 mls of deionized water. This sodium carbonate-deionized water solution is capable of completely dissolving a large amount of TSC (around 10 mg/ml)—which is remarkable considering the hydrophobicity of the carotenoid portion of the BTCS.

A BTCS can be supplied as a powder along with a sterilized bottle of the sodium carbonate water. This concentrated solution can then be injected directly (very small volumes of solutions having a lower ionic strength than plasma can be injected), or the concentrated solution can be added to normal saline and then injected. If TSC is dissolved in the sodium carbonate-water solvent and then more of the same solvent is added—the TSC stays in solution.

In another embodiment, sodium bicarbonate is used instead of sodium carbonate. Other salts which result in the deionized water having a basic pH can also be used.

Carotenoid skeleton concentrations of 5-10 mg/ml can be achieved with this procedure.

Water Dissolves BTCS

Although TSC dissolves in water (tap, distilled, deionized), these solutions are only stable if the pH is adjusted so as to make the solution basic. TSC is more soluble in deionized water (very few $Na^+$ ions present) than in normal water. A BTCS, such as TSC, will dissolve in just deionized water alone, but, if plain deionized water is added to that solution, the TSC will precipitate out. A BTCS will dissolve in just deionized water alone, but additional deionized water may cause precipitation of the BTCS if the pH is not adjusted to make it slightly basic.

Other Methods of Solubilizing BTSC

The BTCS can be formulated in a delivery system that enhances delivery. See Formulations of the Compounds of the Invention below.

Synthesis of the Compounds of the Invention

Bipolar Trans Carotenoid Salts

Set forth below are the novel synthesis methods that can be used for synthesizing bipolar trans carotenoid salts. There can be variations in various steps of the synthesis that are obvious to one skilled in the art.

A. TSC Synthesis

Trans sodium crocetinate (TSC) can be synthesized by coupling a symmetrical $C_{10}$ dialdehyde containing conjugated carbon-carbon double bonds (2,7-dimethylocta-2,4,6-triene-1,8-dial) with [3-carbomethoxy-2-buten-1-ylidene] triphenylphosphorane. This results in the formation of a trans dimethyl ester of crocetin. This dimethyl ester is then converted to the final TSC product by saponification. Typically, saponification is accomplished by treating an ester with either aqueous sodium hydroxide or sodium hydroxide dissolved in THF (tetrahydrofuran); however, these methods did not give the best results in this case. Saponification can be accomplished very well, in this case, by reacting the ester with an NaOH/methanol solution. After saponification, the TSC is recovered by drying in a vacuum.

The $C_{10}$ dialdehyde and the triphenylphosphorane reactants used in this synthesis can be made via different routes. For example, the $C_{10}$ dialdehyde was prepared starting with ethyl bromoacetate and furan using Wittig chemistry. Tiglic acid was the starting material for making the desired phosphorane. Different lengths of carotenoid skeletons can be made by joining together reactants of different lengths (for example a C14 dialdehyde and triphenylphosphorane). This procedure results in the formation of different trans bipolar carotenoid salts. Alterations can also be made so as to obtain different pendant groups (TSC has methyl groups for the pendant groups).

The TSC made in this manner is soluble in water (pH adjusted to 8.0 with a very dilute solution of sodium carbonate) at a level >10 mg/ml at room temperature. Other bipolar trans carotenoid salts are soluble at room temperature in water having a pH that is neutral or above. As used herein, "soluble" means that amounts greater than 5 mg will dissolve per ml of water at room temperature (as noted previously, carotenoid references state that 0.4 mg/ml is "highly significant solubility"—but that is lower than the subject definition of solubility).

B. General Synthesis

Carotenoid or carotenoid related structures can be built up in the following manner:

dehyde (U.S. Pat. No. 5,107,030 does not note this mixture). In the method of the subject invention described in Example 1, 96-97% of the desired isomer (all trans or E,E,E-isomer) is obtained by several recrystallizations from methanol or ethyl acetate in 59% yield.

The improved synthesis method of the subject invention involves converting the remaining isomeric mixture of dialdehydes into the desired trans aldehyde (E,E,E) by isomerization with a sulfinic acid (RSO2H where R is C1 through C10 straight or branched alkyl group or an aryl group (a substituted phenyl group) such as para-toluenesulfinic acid, in an appropriate solvent such as 1,4-dioxane, tetrahydrofuran or dialkyl ether where the alkyl group is one or two of a C1 through C10 straight or branched alkyl group. An additional 8% yield of the pure desired dialdehyde is obtained, raising the overall yield of the last step from 59% to 67% yield. This yield improvement is important. This isomerization step can be incorporated into the third step of the method of U.S. Pat. No. 5,107,030 to get a better yield.

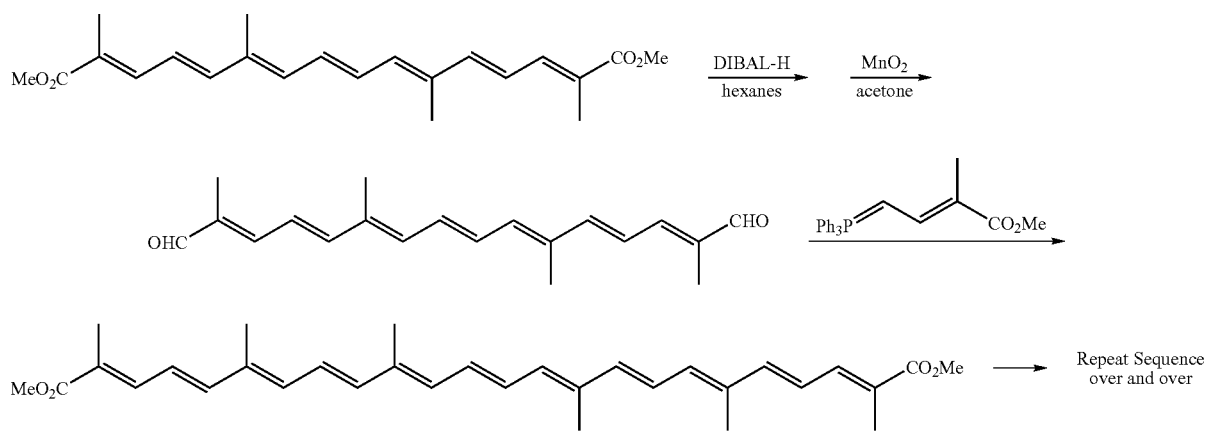

(3-carbomethoxy-2-buten-1-ylidene)triphenylphosphorane (or a related compound when X is other than a methyl group) is a key precursor to add isoprenoid units (or isoprenoid related units) to both ends of a symmetrical carotenoid (or carotenoid related compound). This process can be repeated infinitely. For example, dimethyl trans crocetinate can be reduced to the corresponding, symmetrically dialdehyde using the chemistry described above. This dialdehyde can be reacted with excess (3-carbomethoxy-2-buten-1-ylidene) triphenylphosphorane to give the corresponding diester. This synthetic sequence can be repeated again and again.

Improved Synthesis 2,7-Dimethyl-2,4,6-octatrienedial(2,7-dimethylocta 2,4,6-triene-1,8 dial) is a key intermediate toward the synthesis of TSC. This key precursor has three double bonds and thus several isomers are possible. For TSC, the all trans isomer (E,E,E-isomer) is required. The general synthesis route involves an 11-step synthesis with relatively low yields and poor selectivity in several steps (see Example 1). As a result, column chromatography is required to purify several intermediates along the way.

The improved synthesis route is much simpler (see the reaction scheme below). The 3-step process as described in U.S. Pat. No. 5,107,030, hereby incorporated by reference in its entirety, gives a mixture of geometric isomers of the dial- Improved Synthesis Route:

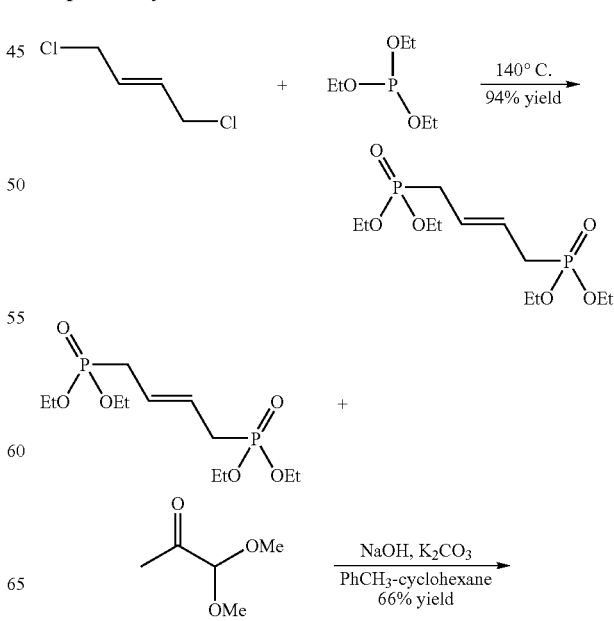

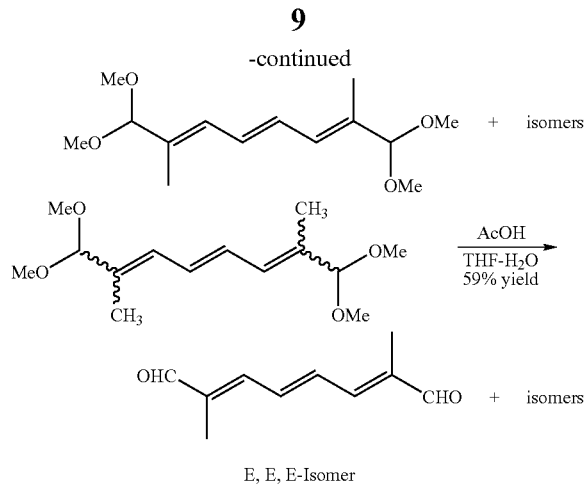

E, E, E-Isomer

Two Undesired Isomers:

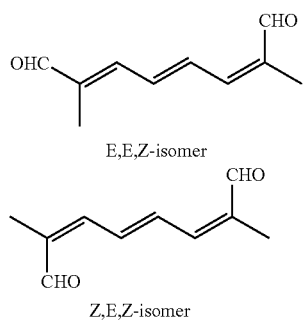

E,E,Z-isomer

Z,E,Z-isomer

Isomerization of Undesired to Desired Dialdehdye:

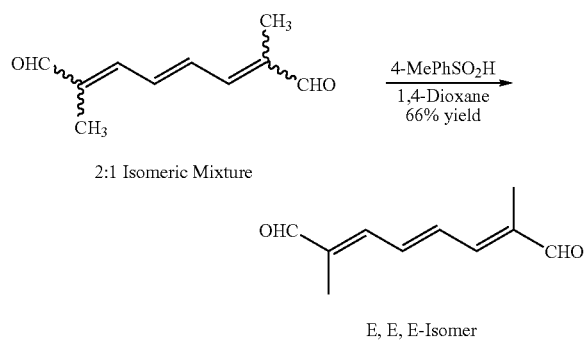

2:1 Isomeric Mixture

E, E, E-Isomer

Saponification can be accomplished by dissolving the diester in methanol and then adding a base such as NaOH (Y of the BTCS is then Na$^+$). Alternatively, the diester can be dissolved in methanol already containing the base. The NaOH is typically aqueous (20-60% by wt.) but can be solid. Alternatives to methanol for dissolving the diester are ethanol, propanol and isopropanol. Saponification can be carried out in various ways commercially. A one or two phase system (one organic and one aqueous phase) can be used.

Trans crocetin can also be synthesized according to the methods described above.

In addition, as has been reported for TSC, such BTCS compounds increase the diffusivity of oxygen through water (this will also depend on the nature of the hydrophobic portion incorporated into the final product such as carbon chain length) since it is believed that the hydrophobic interactions of the carotenoid skeleton with water result in the increased diffusivity).

Formulations of the Compounds of the Invention

A concentrated solution of a bipolar trans carotenoid salt can be made, as described previously, by dissolving it in a very dilute solution of sodium carbonate. The resulting mixture can then be used in that manner, or can be diluted further with normal saline or other aqueous solvents. In addition, solutions of a bipolar trans carotenoid salt can be made by dissolving the bipolar trans carotenoid salt directly in a salt solution and then getting rid of any material that does not dissolve.

The bipolar trans carotenoid salts are stable in a dry form at room temperature, and can be stored for long periods. Advantageously, a formulation of such salts, if given orally, is absorbed in the gut, rather than the stomach.

Although the compounds of the invention can be administered alone, they can be administered as part of a pharmaceutical formulation. Such formulations can include pharmaceutically acceptable carriers known to those skilled in the art as well as other therapeutic agents-see below. Advantageously, the formulation does not include a compound that inhibits the ability of the compounds of the invention to improve diffusivity of oxygen.

Appropriate dosages of the compounds and compositions of the invention will depend on the severity of the condition being treated. For a dose to be "therapeutically effective", it must have the desired effect, i.e. increase the diffusivity of oxygen. This in turn, will cause oxygen-related parameters to return towards normal values.

Administration can be by any suitable route including oral, nasal, topical, parenteral (including subcutaneous, intramuscular, intravenous, intradermal and intraosseus), vaginal or rectal. The preferred route of administration will depend on the circumstances. An inhalation route is advantageous for treatment in emergency situations, where it is necessary for the BTCS to enter the bloodstream very quickly. The formulations thus include those suitable for administration through such routes (liquid or powder to be nebulized). It will be appreciated that the preferred route may vary, for example, with the condition and age of the patient. The formulations can conveniently be presented in unit dosage form, e.g., tablets and sustained release capsules, and can be prepared and administered by methods known in the art of pharmacy. The formulation can be for immediate, or slow or controlled release of the BTCS. See for example, the controlled release formulation of WO 99/15150 hereby incorporated by reference its entirety.

Formulations of the present invention suitable for oral administration can be presented as discrete units such as pills, capsules, cachets or tablets, as powder or granules, or as a solution, suspension or emulsion. Formulations suitable for oral administration further include lozenges, pastilles, and inhalation mists administered in a suitable base or liquid carrier. Formulations for topical administration to the skin can be presented as ointments, creams, gels, and pastes comprising the active agent and a pharmaceutically acceptable carrier or in a transdermal patch.

Formulations suitable for nasal administration wherein the carrier is a solid include powders of a particular size that can be administered by rapid inhalation through the nasal passage. Suitable formulations wherein the carrier is a liquid can be administered, for example as a nasal spray or drops.

Formulations suitable for parenteral administration include aqueous and non-aqueous sterile injection solutions that can contain antioxidants, buffers, bacteriostats and solutes which render the formulation isotonic with the blood of the intended recipient, and aqueous and nonaqueous sterile suspensions which can include suspending agents and thickening agents. The formulations can be presented in unit or multi-dose containers, for example sealed ampules and vials, and can be lyophilized, requiring only the addition of the sterile liquid carrier such as water for injection immediately prior to use. Injection solutions and suspensions can be prepared from sterile powders, granules and tablets.

Uses of the Compounds and Compositions of the Invention

A wide variety of conditions are controlled or are mediated by delivery of oxygen to body tissues. The compounds and compositions of the subject invention can be used in the same pharmaceutical applications described for crocetin in the same effective amounts; see U.S. Pat. Nos. 4,176,179; 4,070,460; 4,046,880; 4,038,144; 4,009,270; 3,975,519; 3,965,261; 3,853,933; and 3,788,468 each of which is hereby incorporated by reference in its entirety.

TSC has been shown to increase the diffusivity of oxygen through aqueous solutions by about 30%. TSC increases survival in mammals following hypoxia, increases oxygen consumption following hypoxia or physiological stress, increases blood pressure following hypoxia, decreases blood acidosis (i.e., decreases blood base deficit, increases blood pH, and decreases plasma lactate level) following hypoxia, decreases organ damage (e.g. liver, kidney) following hypoxia. Thus, the compounds of the invention are useful for treating mammal (including human) diseases/conditions which are characterized by low oxygen (hypoxia) such as respiratory diseases, hemorrhagic shock and cardiovascular diseases, multiple organ failure (due to, for example, ARDS sepsis or hemorrhagic shock), chronic renal failure, atherosclerosis, emphysema, asthma, hypertension, cerebral edema, papillomas, spinal cord injuries, stroke, among others. The compounds of the invention are also useful for treating mammals at risk for the above-noted diseases/conditions. Other bipolar trans carotenoid salts have similar properties. Such compounds can also be used in conjunction with other methods commonly suggested for increasing oxygen utilization in the body, such as oxygen therapy and the use of hemoglobins or fluorocarbons.

In one embodiment of the invention, a BTCS is administered to the patient while administering oxygen. Alternatively, hemoglobins or fluorocarbons and a BTSC can be given together. In these cases, an additive effect is realized.

The minimum dosage needed for treatment for any of these salts is that at which the diffusivity of oxygen increases. The effective dosage of the compounds of the inventions will depend upon the condition treated, the severity of the condition, the stage and individual characteristics of each mammalian patient addressed. Dosage will vary, however, from about 0.001 mg of active compound per kg of body weight up to about 500 mg per kg, and advantageously from about 0.01-30 mg/kg of body weight. IV administration is advantageous but other routes of injection can also be used such as intramuscular, subcutaneous or via inhalation. Oral administration can also be used as can transdermal delivery or intraosseus delivery.

Respiratory Disorders

Bipolar trans carotenoid salts can be used to treat acute and chronic respiratory disorders. These are described as conditions in which the arterial partial pressure of oxygen is reduced, such as value of 60 to 70 mm Hg rather than the normal value of 90-100 mm Hg. Such acute and chronic respiratory disorders include emphysema, acute lung injury (ALI), acute respiratory distress syndrome (ARDS), chronic obstructive pulmonary disease (COPD) and asthma.

TSC increases the value of the partial pressure of oxygen in the blood when it is low (this is a symptom of emphysema, ARDS and COPD). Increasing the partial pressure of oxygen in the blood relieves many of the symptoms of emphysema, ARDS and COPD. TSC does not cure the cause of the disease, but relieves the oxidative distress and damage resulting from that underlying cause.

Hemorrhagic Shock

Hemorrhagic shock is marked by a decrease in oxygen consumption. Bipolar trans carotenoid salts increase the body's oxygen consumption by causing more oxygen to diffuse from the red blood cells to the tissues. TSC has been shown to increase the oxygen consumption of rats undergoing hemorrhagic shock, and has also been shown to offset other symptoms of shock. The compounds of the invention cause the low blood pressure to increase, reduce the increased heart rate, and reverse the blood acidosis that develops during shock. The compounds of the invention also reduce organ damage subsequent to hemorrhagic shock.

The compounds of the invention can be used for hemorrhagic shock by administering them by inhalation, injecting them, or by adding them to a standard resuscitation fluid (Ringer's lactate or normal saline).

Cardiovascular Disease

In western culture, the leading cause of death is ischemic heart disease. Death may result from either a gradual deterioration of the ability of the heart to contract or, frequently, a sudden stoppage. Sudden cardiac death (SCD) covers the time period beginning 60 seconds after symptoms begin to 24 hours later. These deaths are usually a consequence of acute coronary occlusion (blockage) or of ventricular fibrillation (which can result from the occlusion).

Myocardial ischemia exists when there is an insufficient supply of oxygen to the cardiac muscle. When coronary blood flow is extremely low, cardiac muscle cannot function and dies. That area of muscle is said to be infarcted. Most often, diminished coronary blood flow is caused by atherosclerosis that occurs in the coronary arteries. Ischemia results in impaired mechanical and electrical performance and muscle cell injury, which may lead to a lethal arrhythmia, called ventricular fibrillation (VF). In ventricular fibrillation, the electrical activity of the ventricles of the heart is chaotic and results in an electrocardiogram with an erratic rhythm and no recognizable patterns. Ventricular fibrillation occurs frequently with myocardial ischemia and infarction and is nearly always the cause of sudden cardiac death. Bipolar trans carotenoid salts are beneficial in treating myocardial ischemia. Atherosclerosis, which is frequently a precursor to myocardial infarction, and congestive heart failure can also be treated with these salts.

Ischemia

Bipolar trans carotenoid salts are also beneficial in treating other forms of ischemia (insufficient blood flow to tissues or organs) such as kidney, liver, spinal cord, and brain ischemia including stroke.

Surgery

Surgery frequently involves either blood loss or clipping of arteries (e.g., bypass surgery), which can cause ischemia. Bipolar trans carotenoid salts are beneficial as a pretreatment for surgery, or as a treatment during or after surgery.

Hypertension

Hypertension, or high blood pressure, is frequently associated with cardiovascular disease. The compounds of the invention can be used to reduce blood pressure.

Performance Enhancement

BTCS enhance aerobic metabolism, increasing oxygen consumption levels during walking, running, lifting, etc. Endurance is also increased.

Traumatic Brain Injury

Hypoxia following traumatic brain injury results in increased brain damage. BTCS increase oxygen levels in brain tissue after impact injury (focal or diffuse injury). Examples of impact injury include car/motorcycle accidents and falls. BTCS also augment the amount of oxygen reaching normal brain tissue when hyper-oxygen therapy is used.

Alzheimer's Disease

BTCS increase brain oxygen consumption levels in Alzheimer's Disease, thus alleviating symptoms of Alzheimer's Disease. Blood flow and oxygen consumption decline to level some 30% below that seen in non-demented elderly people Wurtman, Scientific American, Volume 252, 1985.

The increased oxygen consumption levels in the brain created by BTCS also reduce memory loss.

Diabetes

BTCS are useful for treating complications of diabetes such as ulcers, gangrene and diabetic retinopathy. Diabetic foot ulcers heal better with hyperbaric oxygen breathing treatment, M. Kalani et al. Journal of Diabetes & Its Complications, Vol 16, No. 2, 153-158, 2002.

BTCS also help the complication of diabetic retinopathy which is related to low oxygen tension, Denninghoff et al., Diabetes Technology & Therapeutics, Vol. 2, No. 1, 111-113, 2000.

Other Uses

Bipolar trans carotenoid salts can also be used for the treatment of spinal cord injury, cerebral edema, anemia, and skin papillomas. In all cases, they alleviate the condition, making it less severe. It is believed that this results from the increase in oxygen consumption that results from the use of bipolar trans carotenoid salts.

Further, bipolar trans carotenoid salts can be used to increase diffusion of other physiologically important molecules such as glucose, $CO_2$ or NO. BTCS also scavenge oxygen-derived free radicals.

The following Examples are illustrative, but not limiting of the compositions and methods of the present invention. Other suitable modifications and adaptations of a variety of conditions and parameters normally encountered which are obvious to those skilled in the art are within the spirit and scope of this invention.

EXAMPLES

Example 1

Synthesis of Trans Sodium Crocetinate

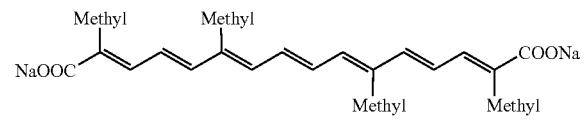

Trans sodium crocetinate is synthesized by coupling a symmetrical $C_{10}$ dialdehyde containing conjugated carbon-carbon double bonds with [3-carbomethoxy-2-buten-1-ylidene]triphenylphosphorane. This product is then saponified using a solution of NaOH/methanol.

To ethyl bromoacetate, trephenylphosphine dissolved in ethyl acetate (at a concentration of around 2 moles/liter) is slowly added. After isolation, and treatment with base, the product can be treated with methyl iodide, followed by caustic, to form the phosphorane. The basic compound to form the carotenoid skeleton can be made starting with a ring compound such as furan in this case. Furan is reacted with bromine and methanol, followed by a selective deprotonation step to form a monoaldehyde. This is then coupled with the phosphorane. Acidic conditions deprotected the other dimethyl acetal group to afford the free aldehyde. This compound is then reacted again with the same phosphorane to give the diethyl diester. The ester groups are reduced to alcohols, and subsequent oxidation (such as with $MnO_2$) results in the $C_{10}$ skeleton in the dialdehyde form. This is later reacted with a phosphorane made from tiglic acid. The tiglic acid is esterified with methanol under acidic conditions to give the methyl ester, followed by a bromination step. The resulting allylic bromide isomers are formed, and can be separated using crystallization. Subsequent treatment of the desired bromide with sodium hydroxide results in the desired phosphorane. This phosphorane and the $C_{10}$ dialdehyde are then dissolved in a solvent such as toluene or benzene and refluxed. The resulting product isolated as a powder and is then saponified with a 40% NaOH/methanol mixture to form the TSC after solvent removal.

Trans-sodium crocetinate 1 (TSC) was prepared in a 17 step synthetic sequence in an overall yield of 1.5%. A total of 4.1 g of TSC was prepared with ethyl bromoacetate, furan- and tiglic acid as starting materials.

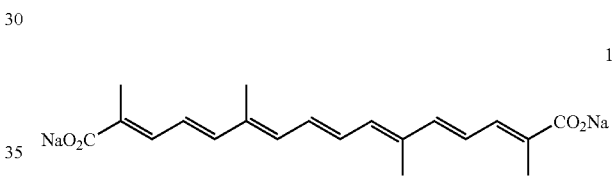

Trans-sodium crocetinate (TSC) was synthesized from saponification of dimethyl crocetinate, the preparation of which was based on a total synthesis reported by Buchta and Andree.[1] The synthetic strategy behind preparing dimethyl crocetinate was based on coupling the symmetrical $C_{10}$ dialdehyde(2,7-dimethylocta-2,4,6-triene-1,8-dial) with (3-carbomethoxy-2-buten-1-ylidene)triphenylphosphorane.

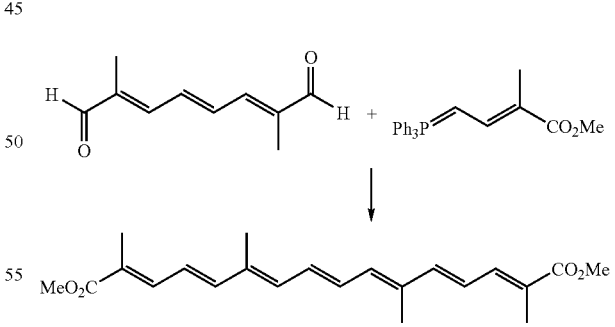

Although the original Buchta and Andree article[1] was titled "The Total Synthesis of trans-2,2-Bisdimethyl-crocetin-dimethyl ester and trans-Crocetin-dimethyl ester," experimental details and yields were not reported. Procedures for the various steps leading to the $C_{10}$ dialdehyde and phosphorane were found after an extensive survey of the literature. Ultimately, TSC was prepared in a 17 step sequence with ethyl bromoacetate, furan and tiglic acid as the starting materials in an overall yield of 1.5%.

The C₁₀ symmetrical dialdehyde was prepared from ethyl bromoacetate² and furan³ using Wittig chemistry. Ethyl bromoacetate was treated with triphenylphosphine and methyl iodide to give the phosphorane 6:

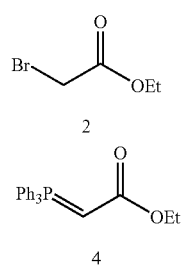

a. TPP, EtOAc, 92%;
b. 1N NaOH, CH₂Cl₂;
c. CH₃I, CH₂Cl₂;
d. 1N NaOH, CH₂Cl₂.

The yield for the first step was a respectable 92%. Quantitation of the subsequent steps of this sequence were complicated by the nature of phosphorane 4 and phosphonium salt 5. Both of these compounds were extremely viscous syrups which foamed vigorously while concentrating on a rotary evaporator. Both compounds could be conveniently handled as methylene chloride solutions and the overall yield of phosphorane 6 appeared to be acceptable from a qualitative point of view (estimated at better than 75%).

Furan was ring-opened with bromine to afford fumaraldehyde bis(dimethylacetal) 8.³

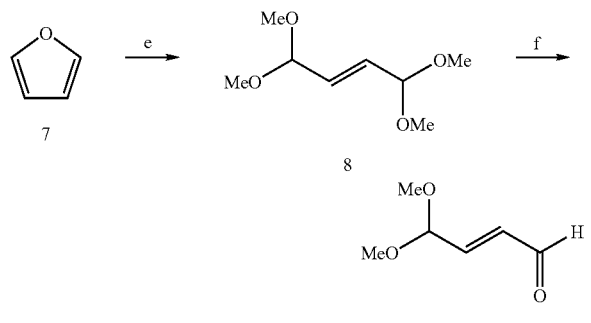

e. Br₂, MeOH; Na₂CO₃, 77%;
f. Amberlyst 15, H₂O, acetone, 72%.

Mono-deprotection of bis(dimethylacetal) 8 under acidic conditions⁴ gave aldehyde 9, which was then coupled with phosphorane 6 to give 10 in a 45% yield. Acidic conditions were used to deprotect the dimethylacetal 10. Treating 11 with phosphorane 6 gave diester 12. The ester groups were reduced to alcohols by DIBAL-H and subsequent oxidation with MnO₂ gave the C₁₀ dialdehyde 14. The trans stereochemistry of 14 was determined by NMR data. In particular, the C₂ symmetry of the compound gave the expected 5 resonances in the ¹³C NMR spectrum and the ¹H NMR spectrum showed signals at δ 9.54 (1H), 7.07 (2H) and 1.95 (3H).

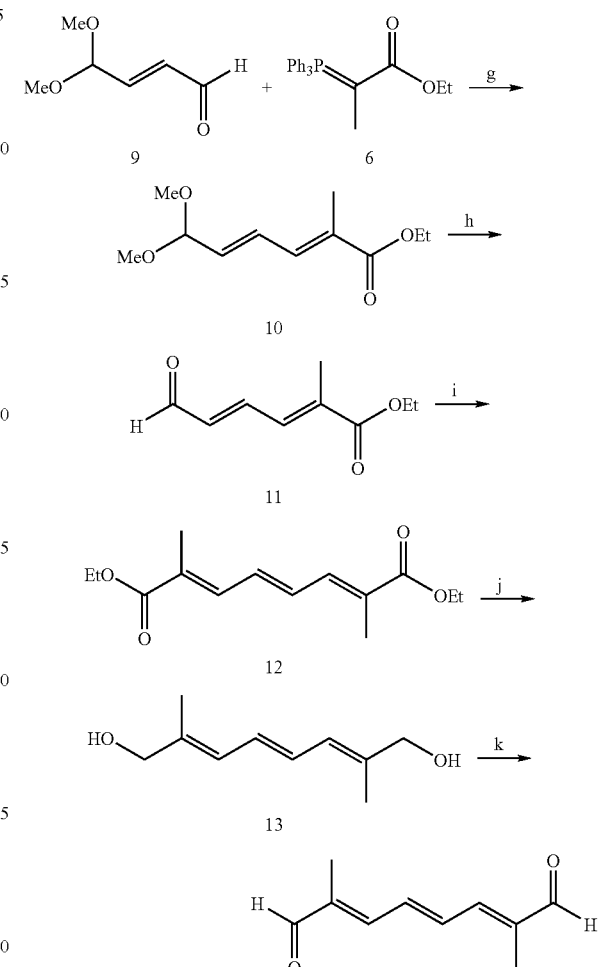

g. CH₂Cl₂, 45%; h. Amberlyst 15, H₂O, acetone, 42-65%; i. 6, CH₂Cl₂, 50-81%; j. DIBAL-H hexanes, 75-81%; k. MnO₂, acetone, 26-58%.

The range in yields of steps h-k reflect improvements in isolation from initial pilot studies to scaled up reactions.

Tiglic acid 15 was converted to phosphorane 20 in a 4 step sequence. Fisher esterification conditions on 15 gave the methyl ester 16. Reaction with NBS gave a mixture of 59% methyl γ-bromotiglate 2.6% methyl α-bromotiglate and the balance of the material was unreacted starting material. The formation of regioisomers was expected based on the reported literature.⁵ In the following step, the α/γ mixture of phosphonium salts was recrystallized to give the desired γ-phosphonium bromide 19.⁶ Subsequent treatment with sodium hydroxide gave the phosphorane 20.

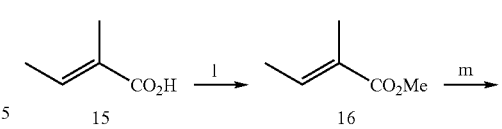

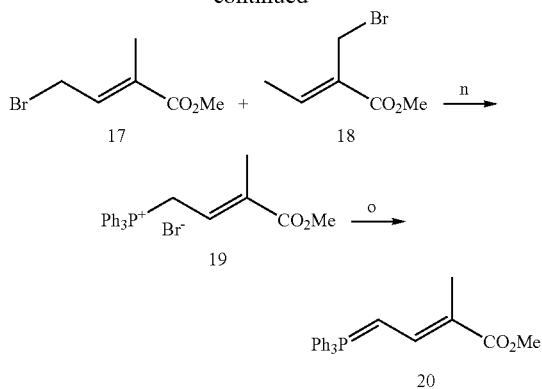

l. $H_2SO_4$, MeOH, 42%; m. NBS, benzoyl peroxide, 59%; n. TPP, $C_6H_6$, 40%; o. NaOH, $H_2O$, 81%

Phosphorane 20 and $C_{10}$ dialdehyde 14 were coupled by refluxing in benzene.[6] Dimethyl crocetinate 21 was isolated as a red powder. Saponification of the methyl ester proved to be more difficult than expected. Treating the ester 21 with 2 eq. NaOH in THF/$H_2O$ at r.t. and reflux left the material unchanged. Solubility appeared to be a significant problem, so pyridine was added. While this did dissolve most of the solids, refluxing a mixture of pyridine and 2.5 N NaOH yielded no product. Standard THF/2.5 N NaOH saponification conditions also had no effect on the ester. Eventually, 40% NaOH/methanol at reflux for an overnight period proved to be successful. This gave TSC 1 as an orange solid.

vents were purchased from Fisher Scientific as ACS reagent or HPLC grade and used without further purification. Anhydrous solvents were purchased from Aldrich in Sure/Seal™ bottles and used directly without further purification. Deionized water was obtained from an in-house Culligan water treatment system.

Melting points were obtained on a Mel-Temp II and were uncorrected. Infrared spectra were measured on a Perkin-Elmer 1600 FTIR spectrophotometer. Nuclear magnetic spectra were measured on a JEOL FX90Q spectrometer using a 5 mm multinuclei probe with internal or external deuterium lock depending on the nature of the sample. Proton and carbon NMR chemical shifts were assigned relative to TMS or the deuterated solvent respectively.

Phosphorus NMR spectra were generally run in the proton-decoupled mode with a coaxial insert tube of 5% aqueous phosphoric acid as the external standard.

Routine analyses by gas chromatography to evaluate reaction progress or estimate product composition were conducted on a Varian 3700 gas chromatograph equipped with a flame ionization detector and a Hewlett Packard 3394A integrator. A 1 microliter solution was injected onto a 15 meter DB5 column (0.53 mm ID and 1.5 micron film thickness) with helium carrier gas using a temperature program from 50 to 250° C. at 20° C./min with a 10 minute hold at 250° C. The injector and detector temperatures were typically set at 250° C.

Thin layer chromatography was conducted on Baker-flex 2.5×7.5 cm silica gel plates with or without fluorescent indicator (1B2 or 1B2-F) depending on the method of detection. The components on the developed plates were detected by UV.

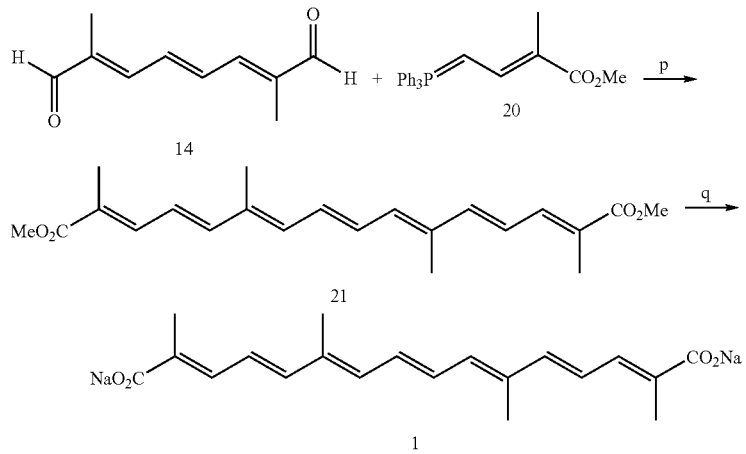

p. $C_6H_6$, reflux, 33-38%; q. MeOH, 40% aq. NaOH, 58-65%.

Attempts were made to dissolve TSC in order to obtain a $^1$NMR spectrum. However, TSC was practically insoluble in most common organic solvents (chloroform, DMSO, pyridine, methanol, acetone, and glacial acetic acid). The TSC produced from this project was characterized by IR, UV, HPLC and elemental analyses. IR showed characteristic absorbance at 1544 and 1402 cm$^{-1}$ (consistent with conjugated carboxylates). UV and HPLC were consistent with authentic TSC.[7] Elemental analyses gave satisfactory values.

The overall yield of the reaction sequence was 1.5% (based on furan).

The synthesis is described in detail below:

All reagents and chemicals were purchased from Aldrich or Sigma and used as received unless stated otherwise. Sol- Elemental analyses were conducted by Quantitative Technologies, Inc., Whitehouse, N.J.

[(Ethoxycarbonyl)methylene]triphenylphosphorane (4)[2] (ACL-G29-1)

Triphenyl phosphine (235.6 g, 0.90 mol) was dissolved in EtOAc (540 mL). Approximately 30 min was required for all of the solids to dissolve. The process was endothermic (solution cooled to 13° C. when the ambient temperature was 20° C.). A solution of ethyl bromoacetate (100 mL, 0.90 mol) in EtOAc (400 mL) was added dropwise over a 1.5 h period. A white precipitate formed during the addition. Stirred overnight (20 h) at ambient temperature (18° C.).

The solids were collected by vacuum filtration rinsing with copious amounts of Et$_2$O. Dried overnight in vacuo at 45° C. to give 3 as a white solid 356.3 g, 92.6% yield (0.83 mol). $^1$H NMR was consistent with literature values.

The solid was dissolved in methylene chloride (3 L) and treated with 1 M NaOH (3.6 L) in a 12 L flask with vigorous stirring for 45 min. The organic layer was separated and the aqueous phase was extracted with additional methylene chloride (2×1 L). Organic layers were dried (MgSO$_4$) and concentrated until approximately 1 L of volume remained. A small amount of material was removed and examined by $^1$H NMR and found to be consistent with literature values.

[1-(Ethoxycarbonyl)ethylidene]triphenylphosphoniun iodide (5)[2] (ACL-G29-2)

The material from ACL-G29-1 was treated with iodomethane (64.0 mL, 1.03 mol) as the reaction flask was cooled in an ice bath. The reaction mixture was checked by TLC (silica gel, 10% MeOH/CHCl$_3$) when the addition was completed (1 h) and it showed a considerable amount of starting material remained. The ice bath was removed and the reaction mixture was checked by TLC after 1.5 h, it looked complete based on a tightening of the main band (s.m. streaked). The reaction mixture was concentrated on a rotary evaporator, when most of the solvent was removed, the product began foaming and creped up the vapor duct. The phosphonium salt 5 appeared was an extremely viscous syrup which was kept as a methylene chloride solution to facilitate handling. Because of the nature of 5, the material was not quantitated.

[1-(Ethoxycarbonyl)ethylidene]triphenylphosphorane (6)[2] (ACL-G29-2A)

A portion of 5 dissolved in CH$_2$Cl$_2$ (350 mL) and vigorously stirred with 1 M NaOH (500 mL) for 45 min. The organic layer was separated and the aqueous was extracted with CH$_2$Cl$_2$ (2×100 mL). Combined organic layers were dried (MgSO$_4$) and concentrated to give 6 as a yellow solid, 8.0 g. $^1$H NMR spectrum was consistent with literature values.

Fumaraldehyde bis(dimethylacetal) (8)[3] (ACL-G29-3)

A solution of furan (88.0 g, 1.29 mol) in anhydrous MeOH (650 mL) was cooled to −45° C. under N$_2$. A solution of bromine (68.0 mL, 1.32 mol) was added dropwise over a 2.5 h period at a rate to maintain ≦−45° C. The red solution was allowed to warm to −10° C. over a 2.5 h period and held for an additional 2 h. The reaction mixture was a pale amber color. Addition of 5 g Na$_2$CO$_3$ produced a considerable amount of outgassing and a 4° C. exotherm. The reaction mixture was cooled with dry-ice and the remaining Na$_2$CO$_3$ (210 g total) was added over a 50 min period. After holding at −10° C. overnight (11 h, the cooling bath was removed and the reaction mixture was allowed to warm to room temperature and stirred for 20 h.

The salts were removed by vacuum filtration and the filtrate was vacuum distilled with a vigreux column until approximately 150 mL had been removed. Additional salt had precipitated out and was causing the distillation pot to bump violently. After filtration, another 150 mL was distilled and more salt came out of solution. Once again, severe bumping was a problem. The still pot was cooled, filtered, the filtrate treated with Et$_2$O (400 mL) and the precipitate removed by vacuum filtration. At least 120 g of salt was collected (early crops of salt were discarded without quantitation). The majority of the Et$_2$O was removed on a rotary evaporator at 25° C. with a water aspirator. Distillation was resumed with a vigreux column, 8 was collected as a clear, colorless liquid 175.2 g (76.9% yield), b.p. 86-92° C./9 torr (lit. 85-90 C/15 ton). $^1$H NMR spectrum was consistent for the desired product. GC analysis: 81.9% pure.

Fumaraldyhyde mono(dimethylacetal) (9)[4] (ACL-G29-4)

Fumaraldyhyde bis(dimethylacetal) 8 (5.29 g, 0.03 mol) was dissolved in acetone (120 mL). H$_2$O (1.80 mL) and Amberlyst 15 (1.20 g) were sequentially added. The mixture was stirred vigorously for 5 min then filtered to removed the resin. During this time, the solution turned from colorless to yellow. The filtrate was concentrated on a rotary evaporator at room temperature and the light brown residue was distilled on a kugelrohr (37° C./200 millitorr) to give 9 as a yellow liquid, 2.80 g, 71.8% yield. A small amount of material was lost when the still pot bumped at the beginning. $^1$H NMR spectrum was consistent for the desired product, GC analysis indicated 80% purity.

(ACL-G29-7)

Fumaraldyhyde bis(dimethylacetal) 8 72.1 g, 0.41 mol) was dissolved in acetone (1600 mL). H$_2$O (25.0 mL) and Amberlyst 15 (16.7 g, prewashed with acetone) was added. The mixture was stirred vigorously for 5 min then filtered to removed the acid resin. The reaction mixture had a slight yellow tint, much fainter than the previous large scale prep. GC analysis indicated 34.5% product and 46.1% s.m. Treated with resin for another 5 min. GC analysis indicated 59.5% product and 21.7% s.m. Treated with resin for another 10 min (total time 20 min). GC analysis indicated 73.9% product and 2.0% s.m. The filtrate was concentrated on a rotary evaporator at room temperature to give a brown oil, 54 g. Vacuum distillation gave a yellow-green oil, 34.48 g. GC analysis indicated 64.7% purity (8.22 min) with a major impurity of 17.5% (9.00 min) and 6.9% (9.14 min). Net recovered yield 22.3 g (0.17 mol). Analysis of the forecut by GC showed extremely dirty material.

(ACL-G29-13)

Amberlyst 15 (8.61 g) was stirred in acetone (100 mL) for 30 min and collected by filtration. The acetal 8 (35.0 g, 0.16 mol) was dissolved in acetonitrile (620 mL) and while mechanically stirred, acid resin and deionized H$_2$O (10.0 mL, 0.55 mol) was added. The course of the reaction was monitored by TLC (10:3 hexane:Et$_2$O), after 15 min most of the starting material had been converted. After 20 min, only a trace of the dimethyl acetal was detected. The resin was removed by filtration and the filtrate was concentrated on a rotary evaporator at ≦40° C. The crude product was loaded on a Biotage column (7.5×9.0 cm) eluting with 15% Et$_2$O in hexanes to give 19.8 g. 65% yield.

6,6-Dimethyoxy-2-methylhexa-2,4-dienoate (10)[2] (ACL-G29-5)

The ylide 6 (7.80 g, 22 mmol) was dissolved in methylene chloride (65 mL). A solution of fumaraldehyde mono(dimethylacetal) 9 (2.80 g, 17 mmol) was added and the solution was stirred overnight. Solvent was removed at reduced pressure on a rotary evaporator. $^1$H NMR of the crude indicated desired product was present. Upon standing, crystals grew (presumably triphenylphosphine oxide). The solid (14.1 g after drying by vacuum filtration) was slurried in petroleum ether and filtered. The filtrate was concentrated to give a yellow oil with solids precipitated out which was dissolve in methylene chloride (15 mL) and chromatographed on a Biotage 4×7.5 cm column eluting with methylene chloride to give 10 as a yellow oil 1.8 g, 50% yield. $^1$H NMR spectrum of the yellow oil was consistent literature values, however, a trace of methylene chloride remained (0.75 eq) so the material was place on the rotary evaporator for 45 min. Mass was reduced to 1.5 g, 40.6% yield and the methylene chloride resonance disappeared. GC analysis major peak at 12.6 min, 87.5% (50° C., 5 min hold, 20° C./min to 250° C. final temperature).

(ACL-G29-6)

A solution of ylide 6 (59.2 g, 0.16 mol) in methylene chloride (650 mL) was cooled in an ice bath and a solution of 9 (25.7 g, 0.19 mol) was added. The solution was stirred overnight allowing the ice bath to melt. TLC (hexane:Et$_2$O 10:3) indicated at least 3 other compounds running very close to the product. Examination of the aldehyde indicated by GC analysis 50.0% purity. Solvent was removed to give a solid/oil mixture.

(ACL-G29-8)

Ylide 6 (59.2 g, 0.16 mol) and acetal 9 (0.19 mol) was coupled in methylene chloride (1.1 L) and worked up as described above to give a yellow-green oil, 80 g. A portion of the crude reaction mixture (4.13 g of the original 80 g) was placed on the kugelrohr and distilled at 50° C./250 millitorr. A colorless oil was condensed 2.28 g, $^1$H NMR indicated it was the starting aldehyde while the product 10 remained in the still pot, 1.85 g. Volatile components were removed from the bulk of the crude product by kugelrohr distillation at 50° C./200 millitorr (net 35 g).

Ethyl 2-methyl-6-oxo-hexa-2,4-dienoate (11)$^2$ (ACL-G29-9)

Acetal 10 from the pilot still pot (ACL-G29-8, 1.85 g, 9 mmol) was dissolved in acetone (33 mL). Deionized H$_2$O (0.50 mL) and Amberlyst 15 resin (0.35 g, prewashed with acetone) were added. The mixture was stirred for 20 min. Filtered and concentrated on a rotary evaporator to give a yellow-green oil, 1.53 g. Chromatographed on a 4.5×7 cm Biotage column eluting with 15% Et$_2$O in hexanes. This system gave incomplete separation, but 0.32 g of the main component was isolated and analyzed; $^1$H NMR spectrum was consistent with literature data and IR (1711, 1682 cm$^{-1}$) was consistent with the desired product. GC 95.6%. An additional 0.35 g was recovered, although it was cross contaminated with less and more polar material. The $^1$H NMR spectrum indicated fairly clean material. GC 90.6%. Yield: 42%.

Diethyl 2,7-dimethylocta-2,4,6-triene-1,8-dioate (12)$^2$ (ACL-G29-10)

The aldehyde 11 (0.65 g, 3.5 mmol) from G29-9 was dissolved and magnetically stirred in methylene chloride. Ylide (1.59 g, 4.4 mmol) was added. The light yellow-green solution turned a darker shade yellow within minutes. TLC after 10 min indicated starting material was almost completely consumed. After stirring for 20 h, the reaction mixture (brown solution) was filtered through a pipette partially filled with silica gel. The filtrate was concentrated to give a brown solid. The solid was dissolved in 5% Et$_2$O in hexanes with a small amount of CHCl$_3$. Chromatographed on a 4×7.5 cm Biotage column eluting with 5% Et$_2$O in hexanes. The main product was isolated as a white crystalline solid, 045 g, 50% yield. $^1$H NMR spectrum was consistent with literature data.

(ACL-G29-14)

An additional amount of 12 was prepared as described above to give 21.8 g, 81.6% after chromatographic purification. $^1$H NMR spectrum was consistent with the desired product.

2,7-Dimethylocta-2,4,6-triene-1,8-diol (13)$^2$ (ACL-G29-11)

The diester 12 (0.45 g, 1.8 mmol) was taken up in anhydrous hexanes (15.0 mL). It appeared as though some of the material dissolved, but the mixture was quite cloudy. More material appeared to come out of solution when the mixture was cooled in a −78 C bath. Neat DIBAL-H (2.50 mL) was dissolved in anhydrous hexanes (total volume 10.0 mL) and a portion (approximately 2 mL) was inadvertently siphoned into the reaction mixture as the diester was cooled in a dry-ice bath. An additional amount of DIBAL-H solution was added until a total of 5.0 mL (6.7 mmol) was added. The CO$_2$ bath was allowed to warm. After stirring for 2 h 50 min, TLC indicated the diester was completely consumed. Bath temperature was adjusted to −20° C. allowing to warm to 0° C. over 20 min. Treated with H$_2$O/silica gel (2 mL/7 g) mixture for 30 min. Added K$_2$CO$_3$ and MgSO$_4$. Filtered to remove the solids and thoroughly rinsed with methylene chloride. Concentrated to give a white solid, 0.14 g, 50% yield. Note: TLC R$_f$=0.21 (5% MeOH/CHCl$_3$) is quite polar. Rinsing with methylene chloride might not have been enough to recover all of the product. $^1$H NMR spectrum was consistent with literature values.

(ACL-G29-15)

The diester (5.4 g, 21 mmol) was taken up in anhydrous hexanes (175 mL, poor solubility), cooled in a −78° C. bath and treated with a solution of DIBAL-H (14.5 mL in 50 mL anhydrous hexanes) over a 35 min period. Vigorous gas evolution was observed during the addition. The color of the slurry went from white to dark yellow initially, this lightened up as additional DIBAL-H was added. Allowed to warm to −40° C. over 2 h, then transferred to a −28° C. bath overnight. The reaction mixture was treated with a homogeneous mixture of H$_2$O/silica gel (4 mL/14.4 g) for 30 min. MgSO$_4$ (7.5 g) and K$_2$CO$_3$ (5.1 g) was added and the reaction mixture was removed from the cooling bath. Stirred 20 min, then filtered on a sintered glass funnel. The solids were washed with methylene chloride—this caused a considerable amount of precipitate to form. Warming while placed on a rotary evaporator dissolved the precipitated solids. The solids remaining on the sintered glass funnel was washed with EtOAc (4×75 mL) and the filtrate was concentrated.

CH$_2$Cl$_2$ rinsings gave a pale-yellow solid, 1.7 g, $^1$H NMR was consistent with literature values; EtOAc rinsings gave an off-white solid, 1.0 g, $^1$H NMR consistent with literature values; total recover 2.7 g, 75% yield.

(ACL-G29-17)

The diester (16.4 g, 6.5 mmol) was stirred in anhydrous hexanes (500 mL) under N$_2$ and cooled to −78° C. A solution of DIBAL-H (45 mL, 253 mmol) in hexanes (150 mL) was added over a 1 h period. Allowed to warm to −30° C. and stirred overnight (17.5 h total time). A homogeneous mixture of $H_2O$/silica gel (12.3 g/43.7 g) was added and the mixture was manually swirled over a 45 min period. Added $K_2CO_3$ (15.5 g) and $MgSO_4$ (23.5 g). Swirled over another 30 min period. Filtered on a sintered glass funnel, rinsed with methylene chloride (ppt formed, presumably caused by evaporative cooling) and the filtrate was concentrated. The solids were rinsed with several times with EtOAc (approximately 100 mL portions, 2 L total volume) and pooled with the original filtrate. Concentrated to give a yellow solid, 8.9 g, 81% crude yield. $^1$H NMR spectrum was consistent with the desired product.

2,7-Dimethylocta-2,4,6-triene-1,8-dial (14)[2] (ACL-G29-12)

A slurry of $MnO_2$ (7.80 g, 90 mmol) was cooled in an ice bath under $N_2$. A solution of diol 13 (0.14 g, 0.8 mmol) was added via pipette as an acetone solution (5.0 mL). An additional 2.0 mL of acetone was used to rinse the flask and complete the transfer. The ice bath was allowed to melt overnight as the reaction mixture was stirred. Solids were removed by filtration through Hyflo and concentrated to give a yellow solid. The material was dissolved in 10% $Et_2O$/hexanes with a minimal amount of $CHCl_3$ and applied to a column of silica gel (30×190 mm) eluting with 10% $E_2O$/hexanes. The product could be followed as a yellow band as it eluted, 14 was isolated as a light yellow solid 37 mg, 26% yield. $^1$H NMR spectrum was consistent literature values.

(ACL-G29-16)

A solution of the diol 13 (2.70 g, 16 mmol) in acetone (500 mL) was cooled in an ice bath under $N_2$. $MnO_2$ (60.0 g, 0.69 mol) was added in portions over a 20 min period. The ice bath was allowed to melt as the reaction mixture was stirred overnight. The reaction mixture was filtered through Hyflo and the filtrate was concentrated to give a yellow solid, 1.6 g, 61% crude yield. $^1$H NMR was consistent with the literature values. The crude yellow solid was dissolved in methylene chloride (along with a small amount of 10% $Et_2O$ in hexanes was added) and charged to a 4×7.5 cm Biotage silica gel column. Eluted initially with 10% ether in hexanes (1 L), then increased polarity to 15% $Et_2O$ (1 L) and 20% $Et_2O$ (0.5 L). Recovered a yellow solid 1.0 g, 38% yield. $^1$H NMR spectrum consistent with desired product.

(ACL-G29-21)

A solution of the diol (9.31 g, 60 mmol) in acetone (500 mL) was cooled in an ice bath under $N_2$. $MnO_2$ (100 g, 1.15 mol) was added and the mixture was stirred as the ice bath was allowed to melt overnight. Checked by IR after 24 h, significant amount of product had formed, but still quite a bit of alcohol present. Added an additional 50 g of oxidant and continued stirring for another overnight period. A portion of the reaction mixture was filtered and checked by $^1$H NMR, the reaction appeared complete based on the consumption of starting material. The rest of the reaction mixture was filtered through a pad of Hyflo and thoroughly rinsed with acetone. Concentrated to give a dark yellow solid. Azeotroped once with 40 mL benzene then dried in vacuo at 40° C. for 5 h, then at r.t. overnight. Recovered 5.28 g, 58% yield. $^1$H NMR and IR spectra were consistent for the desired product.

Methyl Tiglate (16)

In a 2 L 3-neck flask fitted with an overhead stirrer, condenser and thermometer, a solution of tiglic acid 15 (89.8 g; 0.9 mol) and 5 mL concentrated sulfuric acid (0.09 mol) in 900 mL methanol was heated at reflux for 20 hrs. The solution was cooled to 25° C. and the excess methanol was stripped at 30° C. and 27 in Hg vacuum on a rotary evaporator. GLC analysis of the recovered methanol distillate showed product in the overheads. The resulting two-phase, light brown concentrate was taken up in 500 ml ethyl ether and washed successively with 250 mL water, 250 mL 10% aqueous sodium bicarbonate and 250 mL saturated brine. The ether solution was dried over anhydrous potassium carbonate, filtered and stripped on the rotary evaporator at 25° C. and 17 in Hg vacuum to give crude methyl tiglate as a near colorless oil; 43.6 g (42% yield). GLC analysis showed one major volatile product with a retention time of 2.7 min compared to 3.8 min for the starting tiglic acid. Proton NMR in $CDCl_3$ showed the expected signals with some trace ethyl ether contamination: 1.79 ppm (d, 3H), 1.83 (s, 3H), 3.73 (s, 3H), 6.86 (q, 6.6 Hz). IR (neat on KBr): ester carbonyl at 1718 $cm^{-1}$. This oil was used as is in the next step.

Methyl γ-Bromotiglate (17)[5]

In a 1 L 4-neck flask fitted with an overhead stirrer, a thermometer and a condenser, a stirred mixture of the crude methyl tiglate (43.6 g; 0.38 mol), N-bromosuccinimide (68 g; 0.38 mol) and 70% benzoyl peroxide (5.34 g; 0.015 mol) in 500 mL carbon tetrachloride was heated at reflux for two hours. After cooling to 20° C., the insoluble succinimide (38.1 g 100% recovery) was suction filtered off. The filtrate was washed three times with 250 mL water, dried over $MgSO_4$ and then stripped on a rotary evaporator at 25° C. and 26 in Hg vacuum to give a yellow oil; 78.8 g. Proton NMR of this oil in $CDCl_3$ gave a complex spectrum. The methylene protons for the desired γ-bromo ester were assigned to the doublet centered at 4.04 ppm (8.6 Hz), while the same protons for the α-bromo isomer were ascribed to the singlet at 4.24 ppm. Proton integration of these signals and the methyl multiplet from 1.6 to 2.0 ppm suggested the following composition (mole %):
γ-bromo ester: 59%
α-bromo ester: 26%
starting material: 15%
This crude oil was used in the next step without any further purification.

This reaction was also run on a 0.05 mole scale using only 0.87 equivalents of N-bromosuccinimide under otherwise identical conditions. The composition of this crude oil was estimated based on its proton NMR spectrum as 52% γ-bromo ester, 24% α-bromo ester and 23% unreacted methyl tiglate. GLC analysis of this oil was slightly more complicated showing other minor components.

Triphenylphosphonium Salt of Methyl γ-Bromotiglate (19)[6]

In a 2 L 4-neck flask fitted with a thermometer, a 100 mL constant pressure addition funnel and a condenser connected to a static nitrogen system, a stirred solution of the crude methyl γ-bromotiglate (78.8 g) in 350 ml benzene was treated dropwise with a soluton of triphenylphosphine (95 g; 0.36 mol) in 350 mL benzene over a period of 1.75 hrs. The temperature of the mixture exothermed slightly from 24 to 27° C. under otherwise ambient conditions. After the addition, the reaction was stirred vigorously overnight to afford a slurry of white solid containing a yellowish gum that adhered to the walls of the flask. The white solid was suction filtered onto a sintered glass funnel without disturbing the yellowish gum. The flask was washed twice with 100 mL benzene and poured onto the filter. The filter cake was washed with 50 mL benzene and then twice with 50 mL hexane. The wet cake was dried in a vacuum oven at ambient temperature for 5.5 hours. The dried white powder [93 g; mp=125° C. dec)] was dissolved in 150 mL acetonitrile with heat to give a clear yellow solution. Ethyl acetate (300 mL) was added to this hot solution and the product started to crystallized after adding about 100 mL ethyl acetate. The flask was stored in the refrigerator overnight. The product was suction filtered and washed with a minimum amount of 1:2 acetonitrile and ethyl acetate; 45.0 g. mp=187-190° C. (dec). lit mp=183° C. (dec).

The gummy solids in the reaction flask were recrystallized from 10 mL acetonitrile and 20 mL ethyl acetate. Also, additional solids precipitated overnight from the benzene mother liquor. These solids were filtered and recrystallized in the same manner. Both samples were refrigerated for 2 hours and suction filtered to give additonal product; 13.3 g.

The benzene filtrate was stripped on a rotary evaporator and the yellow oil taken up in 10 mL acetonitrile and precipitated with 20 mL ethyl acetate. The slurry was stored in the refrigerator overnight to give additional product as a white solid; 4.6 g. m.p. 185-187° C. (dec). Total yield of the desired phosphonium salt as a white solid was 62.9 g or 36.2% yield based on the crude methyl tiglate. Proton NMR (CDCl$_3$, TMS) ppm 1.55 (d, 4 Hz, 3H), 3.57 (s, 3H), 4.9 (dd, 15.8 & 7.9 Hz, 2H), 6.55 (broad q, 6.6-7.9 Hz, 1H), 7.4-7.9 (m, 15H). Proton-decoupled Phosphorus NMR (CDCl$_3$, 5% aq H$_3$PO$_4$ coaxial external standard) 22.08 ppm. Partial Carbon NMR (CDCl$_3$): CO$_2$CH$_3$, (166.6 ppm, d, $J_{CP}$=3 Hz), olefinic CH (117.5 ppm, d, $J_{CP}$=86.1 Hz), CO$_2\overline{CH_3}$, (52.0 ppm), Ph$_3\overline{P}$—CH$_2$ (25.4 ppm, d, $J_{CP}$=50.6 Hz) and CH$_3$ (13.4 ppm, d, $J_{CP}$=2.4 Hz). Partial IR (KBr pellet): ester carbonyl at 1711 cm$^{-1}$.

(3-Carbomethoxy-2-buten-1-ylidene)triphenylphosphorane (20)[6]

In a 5 L 5-neck flask fitted with an overhead stirrer, an addition funnel and a thermometer, a solution of sodium hydroxide (5.12 g; 0.128 mol) in 250 ml water was added dropwise to a vigorously stirred solution of the triphenylphosphonium salt of methyl γ-bromotiglate (58.3 g; 0.128 mol) in 2,500 mL water over a period of 41 minutes at 25° C. The yellow slurry was stirred for 10 minutes at room temperature and then suction filtered. The filter cake was washed with 1,800 mL water and then thoroughly dried on the filter with a nitrogen blanket. The yellow solid was then dried overnight in a vacuum desiccator over P$_2$O$_5$ at room temperature and 27" Hg vacuum; 35.3 g (73.7% yield). mp=145-150° C. lit mp=145-165° C. Proton-decoupled phosphorus NMR in CDCl$_3$ showed two peaks at 17.1 ppm and 21.1 ppm in a ratio of 93:7. Proton NMR (CDCl$_3$, TMS) ppm 1.89 (s, 3H), 3.58 (s, 3H), 7.3-7.8 (m, 17H). A small but detectable singlet at 1.74 ppm was also apparent in this spectrum which was attributed to the impurity. This solid was used without further purification in the next step.

Dimethyl crocetinate (21)[6] (ACL-G29-18)

The dialdehyde 14 (0.48 g, 2.9 mmol) was added to a 100 mL round bottom flask. Benzene (20 mL) was added and the solids were dissolved with magnetic stirring. The ylide was added, an additional 10 mL benzene was used to wash the compound into the flask. Warmed to a vigorous reflux for 6 h. The reaction mixture was allowed to cool overnight. Contrary to literature reports, a very small amount of solid had formed. The reaction mixture was concentrated, the residue was taken up in MeOH (30 mL) and boiled for 30 min. Upon cooling to ambient temperature, the solids were collected by vacuum filtration. An NMR sample was prepared by dissolving 20 mg into 0.5 mL CDCl$_3$, somewhat surprisingly, this required warming with a heatgun to dissolve completely. $^1$H NMR spectrum was recorded and found to be consistent with the desired product. The remaining material was dissolved in hot benzene, filtered, the filtrate was concentrated, taken up in MeOH, cooled in an ice bath and solids red solids were collected, 334 mg, 33% yield. This material did not appear to be any more soluble than the material which was originally isolated.

(ACL-G29-18A)

Dialdehyde 14 (5.78 g, 35 mmol) was dissolved in benzene (300 mL) under N$_2$. Ylide 20 (35.3 g, 94 mmol) was added and the mixture was warmed to reflux for 6 h forming a dark red solution. After allowing the reaction mixture to cool overnight, red solids were collected by vacuum filtration and rinsed with methanol. Transferred to a 500 mL RBF and refluxed with approximately 65 mL methanol for 30 min. Cooled and collected a red solid. Rinsed with cold methanol and dried in vacuo to give 21 as a red solid, 3.00 g. $^1$H NMR and IR spectra were consistent with the desired product.

The original filtrate (from the reaction mixture) was concentrated on a rotary evaporator and the dark residue was taken up in 100 mL methanol and refluxed for 40 min. Cooled in an ice bath and collected by vacuum filtration a red solid. Rinsed with cold methanol and dried in vacuo to give 21 as a red solid, 1.31 g. $^1$H NMR spectrum was consistent with the desired product.

The filtrates were pooled, concentrated and taken up in 75 mL methanol and allowed to sit overnight at r.t. A red solid was recovered by vacuum filtration: 0.38 g. $^1$H NMR spectrum was consistent with the desired product.

More solids had formed in the filtrate. Isolated by vacuum filtration to give a red solid, 0.127 g. IR consistent with above. Total recovery: 4.89 g, 39% yield.

Saponification Attempt with THF/NaOH (ACL-G29-19)

A stirred suspension of diester 21 (100 mg, 0.28 mmol) in THF (2 mL) and 1N NaOH (0.56 mL, 2 eq) was added. Stirred at r.t. overnight. TLC showed only starting material. Warmed to reflux, no change after several hours. Added THF (6 mL) in an attempt to dissolve more of the solids; but it didn't seem to matter. Continued refluxing overnight. Added more THF (about 6 mL, TLC showed only starting material), and refluxed for another overnight period. Concentrated and check by $^1$H NMR—only starting material (based on integration of the methyls and methyl esters). Dissolved in pyridine (10 mL) while warmed on a heating mantle. Added 2.5 N NaOH (1.0 mL). The dark orange solution turned deep red after several minutes. The heating mantle was removed, solids began forming, mantle reapplied for 30 min, then stirred at r.t. overnight. Concentrated on high vacuum. The residue was insoluble in chloroform, DMSO, pyridine and sparingly soluble in H$_2$O. An IR (Nujol mull) showed C=O absorbance characteristic of the starting material.

Saponification with 2.5 N NaOH and THF
(ACL-G29-20)

Diester 21 (37 mg, 0.10 mmol) was weighed into a flask and stirred in diethyl ether (4 mL). The solvent took on an orange color, but solids were still present. Added 1 mL of 2.5 N NaOH and warmed to reflux. After half an hour, most of the ether had evaporated. This was replaced with THF (3 mL) and refluxing was continued for several hours. Solid were collected by vacuum filtration, rinsed with deionized water then dried in a vacuum oven. IR showed only starting material.

Saponification with 40% NaOH (1) (ACL-G29-22)

Diester 21 (32 mg, 8.9 mmol) was weighed into a flask and stirred in methanol (1.5 mL). The solvent took on an orange/red color, but solids were still present. Added 1.5 mL of 40% NaOH and warmed to reflux for 17 h. After cooling to r.t., orange solids were collected by vacuum filtration and rinsed with deionized water. Dried in vacuo at 40° C. to give 1 as an orange powder 21 mg, 59%. IR (KBr pellet) 3412, 1544, 1402 cm$^{-1}$, the compound is probably hygroscopic, upfield carbonyl shift is consistent with conjugation.

(ACL-G29-22A)

Repeated with 35 mg of diester 1 refluxing for 15 h. The reaction mixture was cooled in an ice bath, collected by vacuum filtration and washed with cold deionized water. Dried in vacuo at 40° C. Recovered 1 as an orange solid 25.5 mg, 65%.

(ACL-G29-23)

Diester 21 (0.48 g, 1.3 mmol) was taken up in methanol (15.0 mL) and 40% sodium hydroxide (15.0 mL) and warmed to reflux. The heterogeneous red mixture turned orange after about 2 h. Heating was discontinued after 6 h and the mixture was allowed to cool overnight. An orange solid was collected by vacuum filtration and washed with cold deionized water. Drying in vacuo gave a friable orange solid, 0.36 g, 68% yield.

(ACL-G29-24)

Diester 21 (1.10 g, 3.1 mmol) was placed in a 100 mL recovery flask and heated to reflux in methanol (20 mL) and 40% NaOH (20 mL) for 12 h. After cooling in an ice bath, an orange solid was collected by vacuum filtration and rinsed with deionized water. Drying in vacuo gave 1.4 g, 100%. Anal Calcd for $C_{20}H_{22}O_4Na_2$-0.4$H_2O$: C, 63.29; H, 6.05; Na, 12.11; $H_2O$, 1.90. Found: C, 63.41; H, 6.26; Na, 11.75; $H_2O$, 1.93.

(ACL-G29-25)

Diester 21 (3.00 g, 8.4 mmol) was refluxed in methanol (80 mL) and 40% NaOH (60 mL) for 12 h. The product was isolated as an orange solid as described above 2.7 g, 80%. Anal Calcd for $C_{20}H_{22}O_4Na_2$-0.4$H_2O$: C, 63.29; H, 6.05; Na, 12.11; $H_2O$, 1.90. Found: C, 63.20; H, 6.00; Na, 11.93; $H_2O$, 1.81. Samples ACL-G29-23, -24 and -25 were ground on an agate mortar and combined as ACL-G29-A.

REFERENCES

1. E. Buchta and F. Andree Naturwiss. 1959, 46, 74.
2. F. J. H. M. Jansen, M. Kwestro, D. Schmitt, J. Lugtenburg Recl. Tray. Chim. Pays-Bas 1994, 113, 552.
3. R. Gree, H. Tourbah, R. Carrie Tetrahedron Letters 1986, 27, 4983.
4. G. M. Coppola Syn. Commun. 1984, 1021.
5. D. S. Letham and H. Young Phytochemistry 1971, 10, 2077.
6. E. Buchta and F. Andree Chem. Ber. 1960, 93, 1349.

Example 2

Synthesis of Trans Potassium Norbixinate

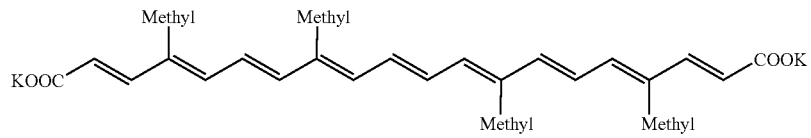

Trans potassium norbixinate is synthesized by coupling a symmetrical C20 dialdehyde containing conjugated carbon-carbon double bonds with [1-(ethoxycarbonyl)methylidene]triphenylphosphorane. The preparation of this compound is similar to that listed previously for trans sodium crocetinate, except that the furan starting material is replaced with the appropriate ringed structure. This product is then saponified using a solution of KOH/methanol.

Example 3

Synthesis of a Longer BTCS

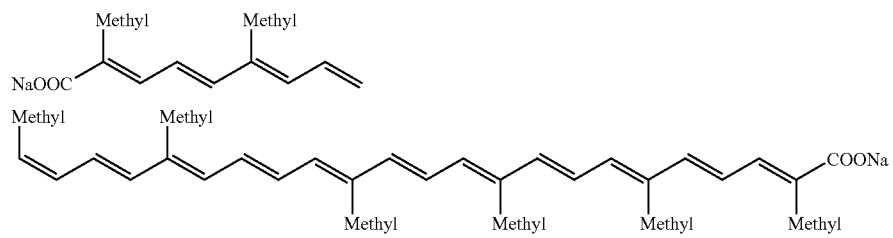

The above compound is synthesized by adding a symmetrical $C_{10}$ dialdehyde containing conjugated carbon-carbon double bonds to an excess of [3-carbomethoxy-2-buten-1-ylidene]triphenylphosphorane. The preparation of this compound is similar to that listed previously for trans sodium crocetinate, except that the furan starting material is replaced with the appropriate ringed structure. The trans 40-carbon product is then isolated using a procedure such as chromatography. This product is then saponified using a solution of NaOH/methanol.

Example 4

TSC by Inhalation

TSC has been given to rats via an inhalation route. Ten rats were given TSC directly into the lungs. This was done by inserting a tube into the trachea, and nebulizing 0.2 ml of TSC solution (TSC dissolved in dilute sodium carbonate solution) with about 3 to 6 mls of air. For all dosages studied (0.5-2 mg/kg), about 20% of the drug was present in the blood stream within one minute after it was given. For dosages of 0.8-1.6 mg/kg the drug was present in the blood stream for a period of at least two hours.

Example 5

Improved Synthesis Method

Prep of Tetraethyl 2-Butenyl-1,4-bisphosphonate

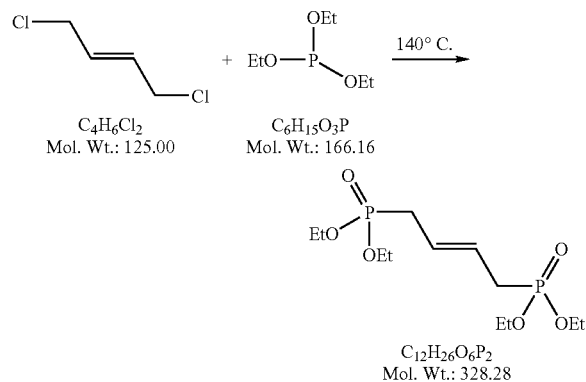

A 250 mL 3-neck flask was equipped with a Teflon-coated thermocouple, a 60 mL constant pressure addition funnel and a simple distillation head. Under a nitrogen atmosphere, neat triethyl phosphite (59 mL; 0.344 mol) was heated with a heating mantle controlled with a JKem controller at 140° C. A solution of trans-1,4-dichloro-2-butene (26.9 g; 0.215 mol) and triethyl phosphite (35 mL; 0.204 mol) was added dropwise at 134-144° C. over a period of 93 minutes. The clear solution was then kept at 140° C. under nitrogen. After 37 minutes, gas chromatography of an aliquot (1 drop) in 1 mL of ethyl acetate showed desired product, intermediate product and the two starting materials.

After 15.5 hrs at 140° C., gas chromatography of an aliquot (1 drop in 0.5 mL EtOAc) showed the desired product with no detectable starting dichloride or intermediate product. After 16 hrs, the faint yellow solution was cooled to room temperature under nitrogen. The faint yellow oil was distilled in a Kugelrohr with a two-bulb receiver and the further bulb cooled in a dry ice-acetone bath at 25-100° C. and 0.1-0.2 torr to give a colorless oil (14.8 g) as a forecut. Gas chromatography showed only product in the Kugelrohr pot. This light amber oil was distilled in a Kugelrohr at 140° C. and 0.1-0.15 torr to give distillate as a colorless oil; 66.45 g (94.1% yield). Gas chromatography showed only one volatile component. GC-MS analysis showed that this component was the desired product, giving a small molecular ion at 328 m/z and a base ion at 191 m/z (loss of $PO_3Et_2$). Proton NMR was consistent with the desired product. Carbon NMR also was consistent with the desired bis(phosphonate diester), showing only long range (W-coupling) and normal carbon-phosphorus coupling to the allylic carbon.

Pot residue—light yellow oil—0.8 g.

Prep of
1,1,8,8-Tetramethyoxy-2,7-dimethyl-2,4,6-ocatriene

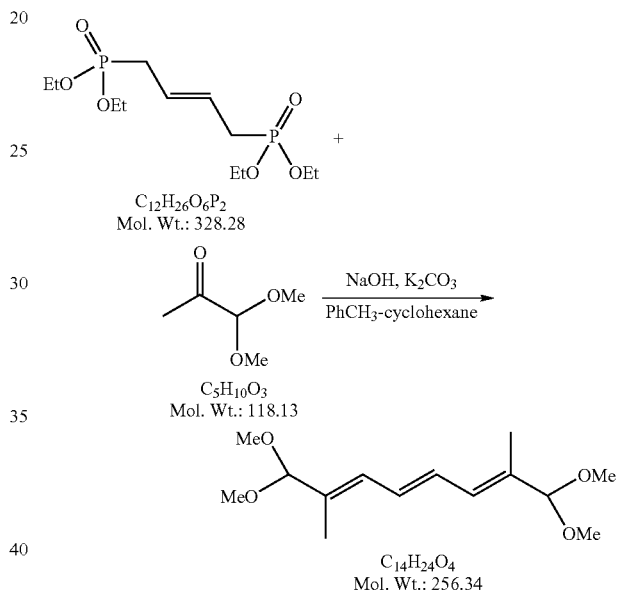

Under a nitrogen atmosphere, a magnetically stirred mixture of tetraethyl trans-2-butenyl-1,4-bisphosphonate (3.3 g; 10.0 mmol), pyruvic aldehyde dimethyl acetal (2.6 mL; 21.5 mmol) in 10 mL toluene and 10 mL cyclohexane was treated successively with anhydrous potassium carbonate (10.2 g; 73.8 mmol) and powdered sodium hydroxide (1.25 g; 31.2 mmol). The solution turned yellow immediately. The resulting slurry was stirred at ambient temperature under nitrogen. The reaction slowly exothermed, reaching a maximum of 38° C. after about 25 minutes. Also, a gummy precipitated formed, which negatively impacted magnetic stirring. After 2.5 hrs, gas chromatography of an aliquot of the yellow-orange solution (1 drop in 0.5 mL toluene) showed the two starting materials and 3 other new components.

After 16.75 hrs at ambient temperature, gas chromatography of an aliquot of the orange solution (1 drop in 0.5 mL toluene) showed only a small amount of the starting bis(phosphonate diester). The resulting orange mixture with a gummy mass (unable to stir) was cooled in an ice bath and quenched with 100 mL 10% aqueous NaCl. The solids were dissolved in this aqueous solution by working with a spatula. The mixture was then extracted with 200 mL 1:1 ether:hexane. The organic layer was washed with 10% aqueous NaCl (200 mL) and then saturated brine (100 mL). The colorless organic layer was dried over $Na_2SO_4$. Gas chromatography showed three major components and no detectable starting bis(phosphonate diester). The thin layer chromatogram showed two major spots and one minor spot. The $Na_2SO_4$ was suction filtered off and washed with ether. The filtrate was concentrated on a rotary evaporator at 35° C. to give a colorless oil; 1.8 g. GC-MS Analysis showed that the three major volatile components were the isomeric products, giving molecular ions at 256 m/z and base ions at 75 m/z [(MeO)$_2$CH$^+$]. Proton NMR also was consistent with a mixture of isomeric products along with other unidentified impurities. Yield of crude product =70.3%.

Prep of
1,1,8,8-Tetramethyoxy-2,7-dimethyl-2,4,6-ocatriene

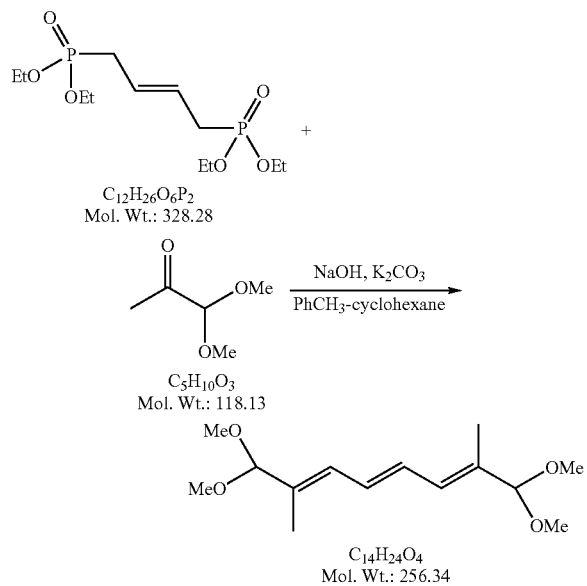

A mechanically stirred mixture of tetraethyl trans-2-butenyl-1,4-bisphosphonate (63.2 g; 0.19 mol), pyruvic aldehyde dimethyl acetal (50 mL; 0.41 mol) in 200 mL toluene and 200 mL cyclohexane was treated successively with anhydrous potassium carbonate (196 g; 1.42 mol) and powdered sodium hydroxide (24.0 g; 0.60 mol). The solution turned yellow immediately. The resulting slurry was stirred at ambient temperature under nitrogen. The reaction exothermed to 61° C. after about 11 minutes and the stirred mixture was cooled in an ice bath to drop the temperature to 35° C. After 4.7 hrs at 29-35° C., gas chromatography of an aliquot (3 drops in 0.5 mL toluene) showed no starting bis(phosphonate). After ≈5 hrs, the mixture was cooled in an ice bath to 13° C. and 10% aqueous sodium chloride (400 mL) was added as the temperature rose to 30° C. More 10% aqueous sodium chloride (1,500 mL) was added and the mixture was extracted with 3,000 mL 1:1 ether:hexane. The tinted yellow organic layer was washed with 10% aqueous sodium chloride (2×1,000 mL) and then with saturated brine (1,000 mL). The tinted yellow organic layer was dried over $Na_2SO_4$, filtered and concentrated on a rotary evaporator at 30° C. to give a light yellow oil; 43.4 g. Gas chromatography showed three major components comprising 89% of the mixture with no detectable starting bis (phosphonate). TLC analysis showed one major and 3 minor components.

Proton NMR showed isomeric product plus toluene. The oil was evaporated further on a Kugelrohr at 50° C. and 0.2 torr for 30 minutes; 31.9 g. Proton NMR showed isomeric bis(acetal) product with no detectable toluene.

Yield =65.5%

Prep of 2,7-Dimethyl-2,4,6-ocatrienedial at Higher Payload

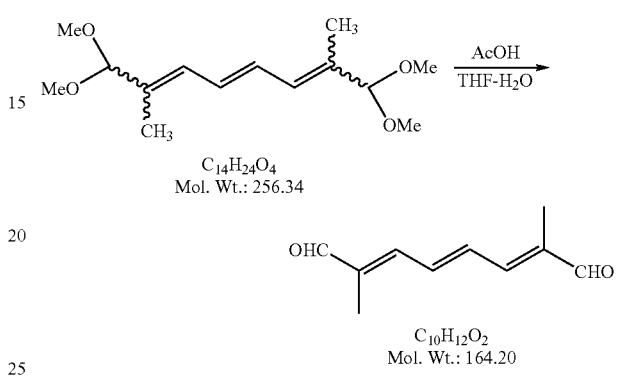

Under a nitrogen atmosphere, a magnetically stirred solution of crude 1,1,8,8-tetramethyoxy-2,7-dimethyl-2,4,6-ocatriene isomers (31.9 g; 124.4 mmol) in tetrahydrofuran (160 mL), water (80 mL) and glacial acetic acid (320 mL) was heated at 45° C. with a heating mantle controlled with a JKem controller via a Teflon-coated thermocouple (9:03 am). After ≈30 minutes, the mixture exothermed to a maximum of 54° C. and then returned to the 45° C. setpoint. Gas chromatography of an aliquot (3 drops in 0.5 mL THF) after 3 hours showed some residual starting material, two major and one minor product. The yellow reaction solution was cooled in an ice bath to 21° C. and then diluted with 4:1 ether:dichloromethane (2,000 mL). This solution was then washed successively with 20% aqueous NaCl (2,000 mL×2), 4:1 20% aq NaCl:1M aqueous NaOH (2,000 mL×3)[1] and 20% aq NaCl (1,000 mL×2). The yellow organic layer was dried over $MgSO_4$, filtered and concentrated on a rotary evaporator to give a yellow solid; 18.9 g. Gas chromatography showed one major and one minor component starting bis(acetal). TLC analysis showed one major spot and several minor, more polar impurities. This solid was dissolved in 250 mL refluxing methanol, cooled to room temperature and then in an ice bath for 1 hr. The slurry was suction filtered to give a yellow fluffy needles; 14.15 g. Gas chromatography showed 95:5 mixture of isomeric dialdehydes. This solid was recrystallized again with 200 mL refluxing methanol, cooled to room temperature and then in the refrigerator overnight.

[1] The first two washes apparently removed acetic acid as evident by neutral pH. The third wash turned red and was still basic, suggesting removal of byproduct.

The slurry was suction filtered and washed with freezer-chilled methanol to give yellow needles; 11.2 g. Gas chromatography showed 97:3 mixture of isomeric dialdehydes. TLC analysis showed one spot. The needles were dried in a vacuum oven at 45° C. for 160 minutes until constant weight; 10.75 g.

uncorrected mp=154-156° C. lit[2] mp=161-162° C. Proton NMR and Carbon NMR were consistent with the desired symmetrical dialdehyde.

[2] Dictionary of Organic Compounds. Verson 10:2, September, 2002.

The two methanol filtrates from the recrystallizations were combined. The thin layer chromatogram showed product plus other impurities. The filtrates were concentrated and various crops collected as shown below.

| Crop | Appearance | Amt (g) | Isomeric Ratio |
|---|---|---|---|
| 2 | yellow powder | 1.4 | 80:20 |
| 3 | yellow needles | 2.6 | 75:25 |
| 4 | yellow solid | 4.45 | 46:30 |

Crop 2 & 3: These combined crops were dissolved in 20 mL refluxing ethyl acetate, cooled to room temperature and then in the freezer for 1 hr. The slurry was suction filtered and washed with freezer-chilled ethyl acetate to give yellow needles; 1.95 g. Gas chromatography showed 86:14 mixture of isomers. This solid was recrystallized again in ethyl acetate (10 mL) to give yellow needles; 1.55 g. Gas chromatography showed 92:8 ratio of isomers. A third recrystallization from ethyl acetate (10 mL) afforded yellow needles; 1.25 g. mp=152-154° C. Gas chromatography showed 96:4 isomer ratio. Proton NMR confirmed as the desired dialdehyde. GC-MS analysis was consistent with the desired dialdehdye, showing a prominent $M^+$ ion at 164 m/z and a base ion at 91 m/z.

The ethyl acetate filtrate was combined with the yellow solid from the methanol filtrate (crop 4) and concentrated on a rotary evaporator to give a yellow solid; 6.0 g. Gas chromatography showed a 53:34 mixture of the two isomers along with other impurities.

The solid was dissolved in 100 mL dichloromethane and Davisil grade 643 silica gel (33.5 g) was added. The mixture was stripped on a rotary evaporator at 35° C. The silica gel with adsorbed material was then added to the sample introduction module for the Biotage system, which already contained a plug of glass wool and a layer of sand. The silica gel was then topped with filter paper. The Biotage 75S column was previously wetted with the solvent mixture with a radial compression of 35 psi and solvent pressure of 20 psi. The column was eluted with 85:15 hexane:ethyl acetate (6,000 mL). A void volume of 1,000 mL including the prewet stage was taken. Fractions of 250 mL were collected and combined based on thin layer chromatogram analysis. These fractions were concentrated on a rotary evaporator at 35° C. as shown below.

| Fraction | Content | Appearance | Amt (g) | Comment |
|---|---|---|---|---|
| 1 | blank | | | |
| 2-3 | A | | | |
| 4 | tr A | | | |
| 5-10 | B | yellow solid | 3.9 | Product Cut |
| 11-18 | tr B or tr C | | | No evidence of close eluting impurity |
| 19-20 | tr B or C & D | | | |

Fractions 5-10: The yellow solid was slurried in hexane and suction filtered to give a bright yellow solid; 2.5 g. Gas chromatography showed an mixture of dialdehyde isomers in a ratio of 67:33.

Total yield of 96-97% E,E,E-dialdehyde=10.75+1.25=12.0 g (58.8% yield).

Isomerization of 2,7-Dimethyl-2,4,6-ocatrienedial with Para-Toluenesulfinic Acid

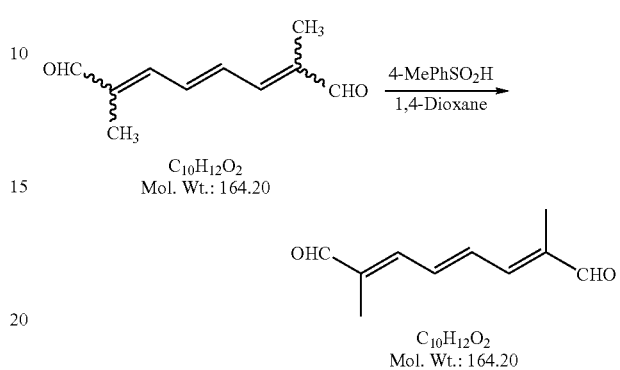

Under a nitrogen atmosphere, the 2:1 isomeric mixture of 2,7-dimethyl-2,4,6-ocatrienedial and its off-isomer (2.5 g; 15.2 mmol) and 4-toluenesulfinic acid (0.35 g; 2.2 mmol) and 50 mL anhydrous 1,4-dioxane was heated at reflux for 15 minutes. An aliquot (7 drops) was diluted in 0.5 mL 4:1 ether:dichloromethane and dried over $K_2CO_3$. Gas chromatography showed a 91:9 mixture of desired isomer and-off-isomer.

After cooling overnight at room temperature, the resulting slurry was dissolved in 100 mL 4:1 ether:dichloromethane and washed successively with water (50 mL×3), 0.2M aqueous NaOH (50 mL), water (50 mL×2) and saturated brine (50 mL×3). After separation of the layers, the remaning rag layer was dissolverl in dichloromethane. The combined organic layers were dried over $MgSO_4$, filtered and concentrated on a rotary evaporator at 40° C. to give an orange solid; 2.2 g. Gas chromatography showed 93:7 ratio of desired dialdehyde to off-isomer. This solid was slurried in hexane and suction filtered to give an orange solid; 2.15 g. This solid was recrystallized from 20 mL refluxing ethyl acetate by cooling to 30-40° C. and then in the freezer for 1 hr. The slurry was suction filtered and washed with freezer-chilled ethyl acetate to give yellow-orange needles; 1.65 g. mp =158-160° C. lit mp=161-162° C. Gas chromatography showed 96:4 ratio of desired dialdehyde to off-isomer. Proton NMR and Carbon NMR were consistent with the desired dialdehdye isomer.

Yield=66%

Scaleup Prep of Methyl Tiglate with Thionyl Chloride in Methanol

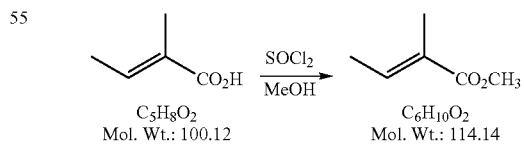

A mechanically stirred solution of tiglic acid (397.35 g; 3.97 mol) in 3000 mL methanol was treated dropwise with neat thionyl chloride (397 mL; 5.44 mol) over a period of 130 minutes as the temperature climbed from 14° C. to a maximum of 50° C. after 80 minutes with no external cooling. Gas chromatography of an aliquot showed complete conversion to the ester with no detectable tiglic acid. After stirring at ambient temperature for 1 hr, the solution was distilled at atmospheric pressure through a silvered, vacuum jacketed Vigreux column (400 mm×20 mm). The condensate was collected at mainly 57-61° C. with a pot temperature of 58-63° C.; 630 mL in 2 hrs. Gas chromatography showed significant methyl ester in the distillate.

The Vigreux column was swapped with a less efficient column (30×2 cm w/less indentations) to speed up the rate of distillation. At a pot temperature of 69-71° C., distillate was collected with a head temperature of 65-69° C.; 1,300 mL over 2.25 hrs. Gas chromatography showed significant methyl ester in the distillate. The atmospheric distillation was continued until the pot temperature reached 87° C., distillate was collected during this period at a head temperature of 69-83° C.; 975 mL over 2 hrs. Gas chromatography showed significantly more methyl ester in the distillate than earlier fractions.

The yellow two-phase mixture in the pot was extracted with ether (300 & 200 mL), dried over $K_2CO_3$, filtered and concentrated on a rotary evaporator at 25° C. to give an orange oil; 132.6 g (29.3% yield). Gas chromatography showed product. Proton NMR and carbon NMR were consistent with the desired product with trace ethyl ether. Gas chromatography of the ether condensate showed some methyl ester in the overheads.

Distillate 3: The third methanol distillate (975 mL) was concentrated on the rotary evaporator at 25° C. to give a two phase mixture (100-150 mL). This mixture was extracted with ether (100 & 50 mL), dried over $K_2CO_3$.

Distillate 2: The second methanol distillate (1,300 mL) was concentrated on the rotary evaporator at 25° C. to give a two phase mixture (30-50 mL). This mixture was extracted with ether (2×50 mL), dried over $K_2CO_3$.

The concentrated ether extracts for distillate 2 and distillate 3 were combined, suction filtered and concentrated on a rotary evaporator at 25° C. to give a colorless oil; 77.3 g.

Proton NMR and carbon NMR matched previous spectra of the desired methyl ester.

Total Yield=132.6+77.3=209.9 g (46.3%)

Alternatively, 1) methyl tiglate is commercially available from Alfa, Lancaster or Acros. and 2), pilots can be run to make phosphonium salt via JOC, 64, 8051-8053 (1999).

Bromination of Methyl Tiglate

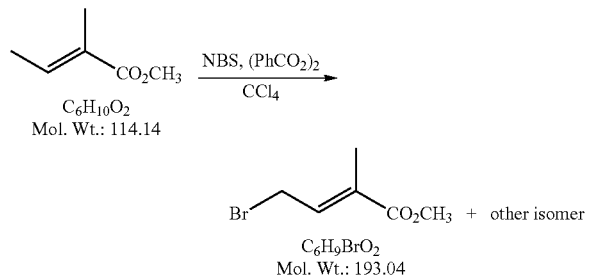

A mechanically stirred slurry of methyl tiglate (209.9 g; 1.84 mol) and N-bromosuccinimide (327.5 g; 1.84 mol), 70% benzoyl peroxide (3.2 g; 0.009 mol) in 2,000 mL carbon tetrachloride was heated to reflux (78-81° C.) with a 1L Kugelrohr bulb between the 5L reaction flask and the reflux condenser. After 2 hrs, reflux was stopped, the mantle dropped and the stirrer shutoff. All of the solids floated on the $CCl_4$ solution, suggesting succinimide with negligible NBS. The slurry was cooled in an ice bath to 20° C. and suction filtered to give an offwhite solid; 180.7 g. No wash. The yellow filtrate was washed with water (1 L×3), dried over $MgSO_4$. Gas chromatography showed starting methyl tiglate and the two monobromides in ≈2:1 ratio along with other minor components.

After filtering off the $MgSO_4$, the light yellow filtrate was concentrated on a rotary evaporator at 35° C. to give a light yellow oil; 327.1 g. Proton NMR and gas chromatography suggested the following composition:

| Component | NMR (mole %) | GC (Area %) |
|---|---|---|
| γ-Bromo | 50% | 49% |
| α-Bromo | 26% | 21% |
| α,γ-Dibromo (?) | 7% | 4% |
| Methyl Tiglate | 6% | 10% |
| Other | 11% | — |

Yield of desired product adjusted for 50% assay=46.0%

This oil is used as is in the next step.

Scaleup Reaction of Methyl γ-Bromotiglate with Triphenylphosphine in Acetonitrile with Slightly Higher Payload

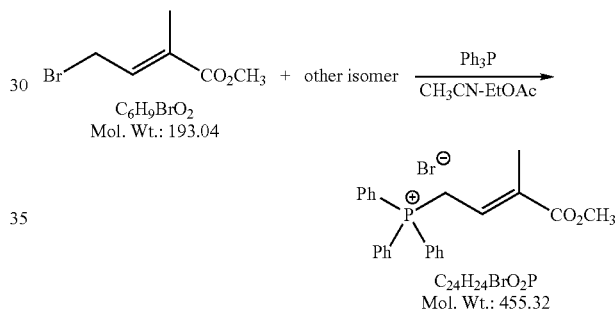

Under a nitrogen atmosphere in a 5 L, 4-neck flask, the crude mixture of methyl γ-bromotiglate (322.6 g; 85% allylic bromide; 1.42 mol) in 1,300 mL anhydrous acetonitrile was stirred mechanically.

A solution of triphenylphosphine (387.0 g; 1.48 mol) in 2,000 mL ethyl acetate was added dropwise over a period of 4 hours. During the addition, the temperature climbed from 22° C. to a maximum of 30° C. after adding about 40% in the first 75 minutes. After adding ≈60% of the triphenylphosphine solution over 120 minutes, the solution became cloudy and continued to precipitate solids through the rest of the addition. After the addition, the funnel was rinsed with ethyl acetate (600 mL) and chased into the reaction mixture. The cream slurry was stirred at ambient temperature over the weekend.

The white slurry was suction filtered and the cake was washed with 2:1 ethyl acetate:acetonitrile (150 mL×3). The white solid (352.55 g) was dried in a vacuum oven at 40° C. for 4 hrs (constant weight after 2 hrs); 322.55 g. mp=187-188° C. (dec). lit mp=183° C. (dec). Proton NMR and Carbon NMR matched previous spectra for the desired phosphonium salt. LC-MS analysis showed one major component, whose electrospray mass spectrum in the positive mode was consistent with the desired phosphonium salt giving a molecular ion at 375 m/z. Phosphorus NMR showed a single phosphorus signal at 22.0 ppm.

Yield based on starting methyl tiglate=100×322.55/(455.32×1.84×322.6/327.1)=39.0%

Prep of (3-Carbomethoxy-2-Z-buten-1-ylidene)triphenylphosphorane

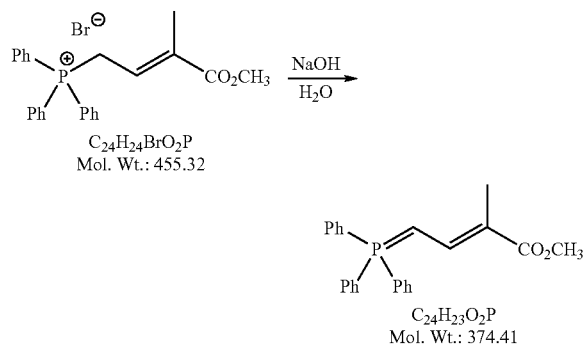

A mechanically stirred slight slurry of (3-carbomethoxy-2-E-buten-1-ylidene)triphenylphosphonium bromide (154.8 g; 0.34 mol) in 3,400 mL deionized water was treated dropwise with a solution of sodium hydroxide (13.6 g; 0.34 mol) in 500 mL water at 23° C. over a period of 32 minutes with no obvious exotherm, but immediate precipitation of a bright yellow solid. After stirring for 15 minutes, the bright yellow slurry was suction filtered, washed with water (1,500 mL) and sucked dry to give a canary yellow solid; 151.7 g. This solid was dried in a vacuum oven at 35-45° C. (3:50 pm) overnight.

After drying in the vacuum oven at 35-45° C. for 22.5 hrs, a constant weight was obtained; 107.8 g. mp=144-160° C. lit mp=145-165° C. Proton NMR was similar to the previous spectrum of the desired ylide considering the differences in NMR field strength. Carbon NMR showed the methyl carbon's at 50.2 and 11.8 ppm with a complex aromatic region and no obvious signals for the olefinic carbons and the ylide carbon.

Yield=84.7%

Pilot Prep of Dimethyl Crocetinate

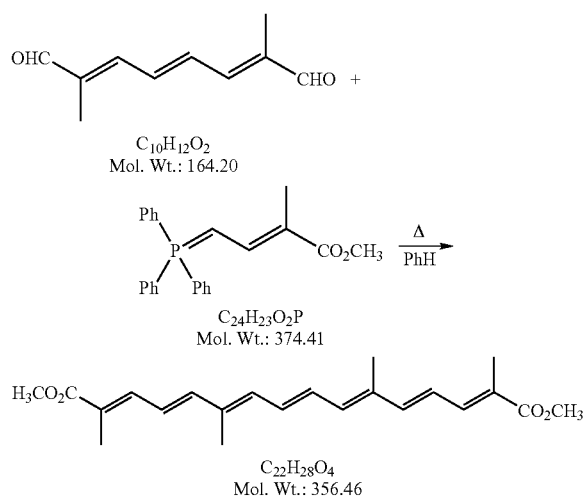

Under a nitrogen atmosphere, a magnetically stirred mixture of (3-carbomethoxy-2-Z-buten-1-ylidene)triphenylphosphorane (12.8 g; 34.2 mmol) and 2,7-dimethyl-2,4,6-ocatrienedial (2.1 g; 12.8 mmol) in benzene (128 mL) was heated to reflux for 6 hrs using a timer.

The resulting slurry was cooled in an ice bath for 40 minutes, suction filtered, washed with benzene and sucked dry to melt the frozen benzene to give a red solid; 2.1 g. TLC analysis showed a single, yellow spot. This solid was dried in a vacuum oven at 40-45° C. for 70 minutes; 1.85 g (40.5% yield). uncorrected mp=210-213° C. lit[3] mp=214-216° C. Proton NMR was similar to the previous spectrum of dimethyl crocetin on 90 MHz instrument. Carbon NMR showed all 11 unique carbon signals with the correct chemical shift for the desired dimethyl ester with one minor impurity signal that may be residual benzene. Electrospray mass spectrum suggested decomposition and recombination of fragments.

[3] E. Buchta Si F. Andree, Chem Ber, 93, 1349 (1960).

TLC analysis showed that the red filtrate contained additional product, triphenylphosphine oxide and an orange component with an $R_f$ slightly lower than the isolated solid. The red filtrate was concentrated on a rotary evaporator at 35° C. to give red solids; 13.2 g. This solid was heated at reflux in methanol (25 mL). The resulting slurry was then cooled in an ice bath, suction filtered after 60 minutes and washed with methanol to give a red solid; 0.6 g. This solid was dried in the vacuum oven at 45° C. 135 minutes; 0.5 g. mp=203-208° C. Proton NMR showed desired diester with residual impurities. Carbon NMR showed only signals for desired product. TLC analysis showed streaky product spot.

Filtrate was concentrated and saved.

Second Prep of Dimethyl Ester of Crocetin

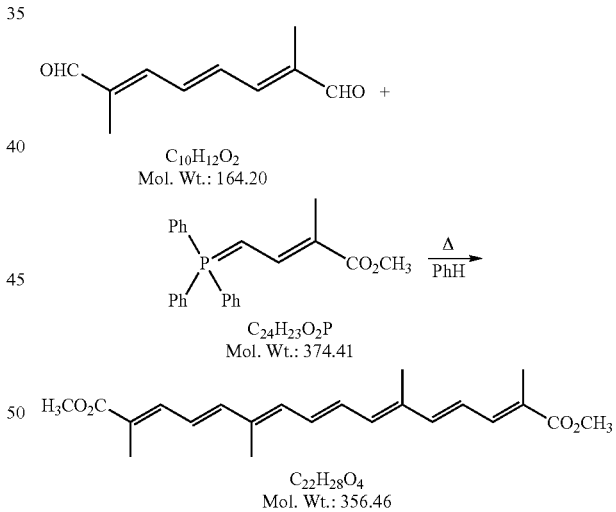

Under a nitrogen atmosphere, 2,7-dimethyl-2,4,6-ocatrienedial (11.95 g; 12.8 mmol) was added in one portion to a mechanically stirred slurry of (3-carbomethoxy-2-Z-buten-1-ylidene)triphenylphosphorane (73.0 g; 195.0 mmol) in 400 mL benzene and then chased with 330 mL benzene. The resulting brown slurry was heated to reflux for 6 hrs using a timer and cooled to room temperature overnight under nitrogen.

The resulting slurry was cooled in an ice bath to 6-10° C., suction filtered and washed with benzene (50 mL×2) to give a red solid; 10.05 g. TLC analysis showed a single yellow spot. This solid was dried in a vacuum oven at 40° C. (9:00 am) for 3.5 hrs with no weight loss; 10.05 g (38.7% yield). mp=211-214° C. lit mp=mp=214-216° C. Proton NMR and Carbon NMR matched the previous spectra for the desired dimethyl ester of crocetin.

The red filtrate was concentrated on a rotary evaporator at 40° C. to give a red solid; 84.4 g. TLC analysis was similar to the pilot run. This solid was slurried in 165 mL methanol at reflux with magnetic stirring. The resulting slurry was then cooled in an ice bath for 2.5 hrs, suction filtered and washed with a minimal amount of methanol to give an orange paste; 10.5 g. TLC analysis showed a single, yellow spot. This paste was dried in a vacuum oven at 45° C. for 190 minutes; 5.6 g. mp=201-208° C. NMR showed desired diester with unknown aromatic impurities.

This impure solid and two other similar solids from earlier runs totaling 6.5 g were dissolved in refluxing chloroform (75 mL) and diluted with methanol and cooled in the refrigerator overnight.

The slurry was suction filtered and washed with a minimal amount of methanol to give red crystalline solid; 6.1 g. This solid was dried in the vacuum oven at 45° C. for 3 hrs until constant weight; 4.25 g. mp=211-213° C. Proton NMR and carbon NMR showed other olefinic or aromatic impurities. The solid was dissolved in refluxing toluene (150 mL) and eventually cooled in the refrigerator for 130 minutes. The slurry was suction filtered and washed with tolene to give a red solid; 2.05 g. This-solid was dried in the vacuum oven at 45° C. for 50 minutes with no weight change; 2.05 g. mp=214-216° C. Proton NMR showed the desired dimethyl crocetin with some residual toluene and negligible off-isomer impurities. Carbon NMR showed the desired dimethyl crocetin with no detectable off-isomer impurities and 2-3 new residual signals that were consistent with toluene. Yield=45.5%.

Prep of Disodium Salt of Crocetin

After a total of 65.5 hrs of drying, amount of orange powder was 23.1 g. The infrared spectrum showed extra bands compared to the reported IR spectrum of TSC, especially large bands at 3424 and 1444 $cm^{-1}$. Proton NMR showed no evidence of methyl esters. However, the integration of the olefinic and methyl regions were off, possibly due to phasing problems.

Assuming that the excess weight was due to sodium hydroxide, the orange solid was stirred magnetically in 400 mL deionized water for 35 minutes. The slurry was suction filtered and the cake washed with deionized water (50 mL×2) to give an orange paste. This material was dried in a vacuum oven at 45-50° C. until constant weight. After about 7 hrs, the solid was crushed and pulverized and dried further in the vacuum oven at 45° C. overnight.

After 21 hrs of drying at 45° C., amount of solid was 13.25 g. After further pulverizing and drying in the vacuum oven at 45° C., amount of solid was 13.15 g. The infrared spectrum was consistent with the reported IR spectrum. Proton NMR gave a proton NMR spectrum that was consistent with The disodium salt. HPLC analysis showed one major component with possibly one minor impurity. The electrospray negative ion mass spectrum of the major component was consistent with the desired disodium salt of crocetin. Carbon NMR showed all ten unique carbon signals for disodium salt of crocetin, verifying the symmetry of the molecule.

The original filtrate of water, sodium hydroxide and methanol precipitated more solids during the water wash. This slurry was suction filtered, washed with water to give an orange paste. This paste was dried in the vacuum oven at 45° C. for 18.5 hrs to give an orange solid; 0.65 g. The spectral data were consistent with the desired disodium salt of crocetin. This solid was combined with the first crop.

Yield=13.15+0.65=13.8 g (94.8%).

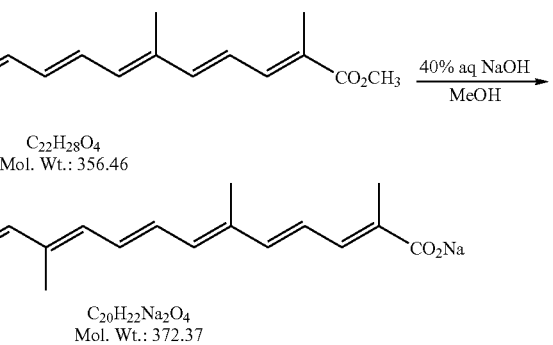

A mechanically stirred slurry of dimethyl crocetin (13.95 g; 39.1 mmol) and 40 wt % aqueous sodium hydroxide (273 mL; 3.915 mol) and methanol (391 mL) was heated at reflux at 74° C. for 12 hrs using a timer.

The orange slurry was suction filtered through a Buchner funnel with filter paper and a sintered glass funnel. Slow filtration.[4] The slurry in the sintered glass funnel was added to the solids in the Buchner funnel. The orange paste was washed with water (100 mL×3) and then with methanol (50 mL×3). The orange paste was dried in a vacuum oven at 45-50° C.

After 21 hrs, the orange clumps weighted 24.25 g. The material was pulverized with a spatula and dried in the vacuum oven at 45-50° C.

Elemental Analyses of the first crop showed unacceptable values for the desired product, suggesting sodium hydroxide contamination of the disodium salt of crocetin.

Water Wash of Disodium Salt of Crocetin

The disodium salt of crocetin (13.6 g) was slurried in 150 mL deionized water and stirred magnetically at room temperature for 1 hr. The slurry was suction filtered onto a Buchner funnel. The orange paste was then washed with water and the pH of the orange filtrate monitored.

The orange paste was sucked dry on the filter with a rubber dam. This paste was dried in a vacuum at 25-55° C. for 5.5 hrs to give a friable orange solid; 11.2 g. This solid was pulverized, transferred to a bottle and dried in the vacuum oven at 45° C. overnight.

[4] Filtered faster through sintered glass until the filter clogged after drying out. However, water wash unclogged the filter.

Amount=11.1 g. Recovery=81.6%. The IR and Proton NMR spectra matched previous IR and proton NMR spectra of the desired disodium salt of crocetin. HPLC analysis showed a single component at 420 nm, whose electrospray mass spectrum in the negative ion mode was consistent with crocetin.

Carbon NMR showed all ten unique carbon signals with the correct chemical shifts for the desired disodium salt of crocetin. Elemental analysis gave acceptable data for the desired product.

REFERENCES

1. *Tetrahedron Letters,* 27, 4983-4986 (1986).
2. F. J. H. M. Jansen, M. Kwestro, a Schmitt & J. Lugtenburg, *Recl. Tray. Chem. Pays-Bas,* 113, 552-562 (1994) and references cited therein.
3. J. H. Babler, U.S. Pat. No. 4,107,030, Apr. 21, 1992.
4. T. W. Gibson & P. Strassburger, *J. Org. Chem.,* 41, 791 (1976) & J. M. Snyder & C. R. Scholfield, *J. Am. Oil Chem. Soc.,* 59, 469 (1982).

Example 6

Purity Determination of TSC Made According to the Improved Synthesis Method

For the TSC material synthesized according to the method of Example 5, the ratio of the absorbance at 421 nm to the absorbance at 254 nm was 11.1 using a UV-visible spectrophotometer.

Example 7

Oral Administration of TSC

TSC has been shown, in rats, to be absorbed into the blood stream when administered orally (via a gavage technique). In two rats, it was found that 1 to 2% of the dosage given was present in the blood stream at a time of 15 to 30 minutes after being given. The maximum amount absorbed orally actually occurred earlier than that time.

It will be readily apparent to those skilled in the art that numerous modifications and additions can be made to both the present compounds and compositions, and the related methods without departing from the invention disclosed.

What is claimed is:

1. A pharmaceutical composition of synthetic trans sodium crocetinate having the structure:

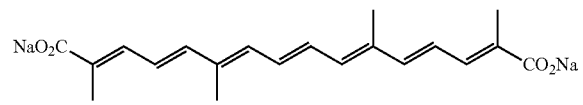

wherein the purity level of the trans isomer in the composition is such that, under UV-visible analysis, the absorbency of the highest peak which occurs in the visible wave length range divided by the absorbency of the peak which occurs in the UV wave length range is greater than 7.5.

2. A composition as in claim 1 wherein the absorbancy of the highest peak which occurs in the visible wave length range divided by the absorbency of the peak which occurs in the UV wave length range is greater than 8.

3. A composition as in claim 1 wherein said composition is in a unit dosage form.

4. A composition as in claim 1 wherein said composition is in a form of a pill, tablet, or capsule.

5. A method of increasing the diffusivity of oxygen in a mammal comprising administering to a mammal a therapeutically effective amount of a bipolar trans carotenoid salt compound having the formula:

where:
Y=a cation
Z=a polar group which is associated with the cation, and
TCRO=trans carotenoid skeleton having pendant groups X, wherein the pendant groups X, which can be the same or different, are a linear or branched group having 10 or less carbon atoms, or a halogen,
wherein said compound is not trans sodium crocetinate.

6. A method of treating a mammal, having a disease or condition characterized by hypoxia, comprising administering to such mammal a therapeutically effective amount of a bipolar trans carotenoid salt compound having the formula:

where:
Y=a cation
Z=a polar group which is associated with the cation, and
TCRO=trans carotenoid skeleton having pendant groups X, wherein the pendant groups X, which can be the same or different, are a linear or branched group having 10 or less carbon atoms, or a halogen,
wherein said compound is not trans sodium crocetinate.

7. A method as in claim 6 wherein said disease or condition characterized by hypoxia is selected from the group consisting of ischemic, traumatic brain injury, respiratory disease, hemorrhagic shock, cardiovascular disease, multiple organ failure, atherosclerosis, emphysema, asthma, hypertension, cerebral edema, and spinal cord injury.

8. A method of increasing the diffusivity of oxygen in a mammal comprising administering to a mammal a therapeutically effective amount of a composition of synthetic trans sodium crocetinate having the structure:

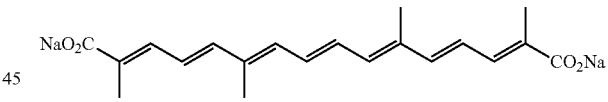

wherein the purity level of the trans isomer in the composition is such that, under UV-visible analysis, the absorbency of the highest peak which occurs in the visible wave length range divided by the absorbency of the peak which occurs in the UV wave length range is greater than 7.5.

9. A method of treating a mammal having a disease or condition characterized by hypoxia comprising administering to such mammal a therapeutically effective amount of a composition of synthetic trans sodium crocetinate having the structure:

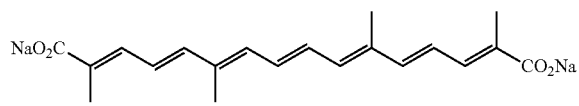

wherein the purity level of the trans isomer in the composition is such that under UV-visible analysis, the absorbency of the highest peak which occurs in the visible wave length range divided by the absorbency of the peak which occurs in the UV wave length range is greater than 7.5.

10. A method as in claim 9 wherein said disease or condition characterized by hypoxia is selected from the group consisting of ischemia, traumatic brain injury, respiratory disease, hemorrhagic shock, cardiovascular disease, multiple organ failure, atherosclerosis, emphysema, asthma, hypertension, cerebral edema, and spinal cord injury.

11. A method of increasing endurance in a mammal during physical activity comprising administering to said mammal a therapeutically effective amount of a bipolar trans carotenoid salt compound having the formula:

YZ-TCRO-ZY where:
Y=a cation
Z=a polar group which is associated with the cation, and
TCRO=trans carotenoid skeleton having pendant groups X, wherein the pendant groups X, which can be the same or different, are a linear or branched group having 10 or less carbon atoms, or a halogen.

12. A method as in claim 11 wherein said physical activity is walking, running, or lifting.

13. A method of increasing aerobic metabolism in a mammal comprising administering to said mammal a therapeutically effective amount of a bipolar trans carotenoid salt compound having the formula:

YZ-TCRO-ZY where:
Y=a cation
Z=a polar group which is associated with the cation, and
TCRO=trans carotenoid skeleton having pendant groups X, wherein the pendant groups X, which can be the same or different, are a linear or branched group having 10 or less carbon atoms, or a halogen.

14. A method of treating anemia in a mammal comprising administering to a mammal in need of treatment a therapeutically effective amount of a bipolar trans carotenoid salt compound having the formula:

YZ-TCRO-ZY where:
Y=a cation
Z=a polar group which is associated with the cation, and
TCRO=trans carotenoid skeleton having pendant groups X, wherein the pendant groups X, which can be the same or different, are a linear or branched group having 10 or less carbon atoms, or a halogen.

15. A method of treating stroke comprising administering to a mammal in need of treatment a therapeutically effective amount of a bipolar trans carotenoid compound having the formula:

YZ-TCRO-ZY where:
Y=a cation
Z=a polar group which is associated with the cation, and
TCRO=trans carotenoid skeleton having pendant groups X, wherein the pendant groups X, which can be the same or different, are a linear or branched group having 10 or less carbon atoms, or a halogen.

16. A method of reducing the amount of ischemia resulting from surgery in a mammal comprising administering to a mammal before, during, or after surgery a therapeutically effective amount of a bipolar trans carotenoid salt compound having the formula:

YZ-TCRO-ZY where:
Y=a cation
Z=a polar group which is associated with the cation, and
TCRO=trans carotenoid skeleton having pendant groups X, wherein the pendant groups X, which can be the same or different, are a linear or branched group having 10 or less carbon atoms, or a halogen.

17. A method of treating a mammal at risk of a disease or condition characterized by hypoxia comprising administering to such mammal a therapeutically effective amount of a bipolar trans carotenoid salt compound having the formula

YZ-TCRO-ZY where:
Y=a cation
Z=a polar group which is associated with the cation, and
TCRO=trans carotenoid skeleton having pendant groups X, wherein the pendant groups X, which can be the same or different, are a linear or branched group having 10 or less carbon atoms, or a halogen.

18. A method as in claim 17 wherein said disease or condition characterized by hypoxia is selected from the group consisting of ischemia, traumatic brain injury, respiratory disease, hemorrhagic shock, cardiovascular disease, multiple organ failure, atherosclerosis, emphysema, asthma, hypertension, cerebral edema, spinal cord injury, and stroke.

19. A method as in claim 5, 6, 11, 13, 14, 15, 16, or 17 wherein Y is a monovalent ion selected from the group consisting of Na+, K+ or Li+, or an organic cation selected from the group consisting of R4N+, R3S+, wherein R is H, $C_nH_{2n+1}$ wherein n is 1-10, Z is selected from the group consisting of a carboxyl (COO—) group, a sulfate group (OSO3-) or a monophosphate group (OPO3-), (OP(OH)O2-), a diphosphate group, triphosphate or combinations thereof, and the TCRO is less than 100 carbons and X is a linear or branched group having 4 or less carbon atoms.

20. A method as in claim 5, 6, 11, 13, 14, 15, 16, or 17 wherein Y is Na+, K+ or Li+, Z is a carboxyl group, and the TCRO is less than 100 carbons and has pendant methyl groups.

21. A method as in claim 11, 13, 14, 15, 16, or 17 wherein said bipolar trans carotenoid salt compound is trans sodium crocetinate.

22. A method as in claim 8 or 9 wherein the absorbency of the highest peak which occurs in the visible wave length range divided by the absorbency of the peak which occurs in the UV wave length range is greater than 8.

23. A method as in claim 5, 6, 11, 13, 14, 15, 16, or 17 wherein said administration is by intravenous route.

24. A method as in claim 5, 6, 11, 13, 14, 15, 16, or 17 wherein said administration is by oral route.

25. A method as in claim 7, 10, or 18 wherein said ischemia is myocardial ischemia.

26. A method as in claim 8, 9, 10, or 22 wherein said trans sodium crocetinate is administered at a dose of 0.01-30 mg/kg.

27. A method as in claim 11, 12, 13, 14, 15, 16, 17, 18, 19, 20, or 21 wherein said compound is administered at a dose of 0.01-30 mg/kg.

* * * * *